(12) United States Patent
Matsumura

(10) Patent No.: US 8,043,216 B2
(45) Date of Patent: Oct. 25, 2011

(54) METHOD OF DISPLAYING ELASTIC IMAGE AND DIAGNOSTIC ULTRASOUND SYSTEM

(75) Inventor: Takeshi Matsumura, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1355 days.

(21) Appl. No.: 11/628,940

(22) PCT Filed: Jun. 9, 2005

(86) PCT No.: PCT/JP2005/010567
§ 371 (c)(1),
(2), (4) Date: Dec. 8, 2006

(87) PCT Pub. No.: WO2005/120358
PCT Pub. Date: Dec. 22, 2005

(65) Prior Publication Data
US 2008/0269606 A1    Oct. 30, 2008

(30) Foreign Application Priority Data

Jun. 9, 2004    (JP) .................................. 2004-170959

(51) Int. Cl.
*A61B 8/00*    (2006.01)
(52) U.S. Cl. ......... 600/438; 600/437; 600/443; 600/440
(58) Field of Classification Search ............. 600/437, 600/438, 443, 440, 441
See application file for complete search history.

(56) References Cited

U.S. PATENT DOCUMENTS

| | | | |
|---|---|---|---|
| 6,511,427 B1 | 1/2003 | Sliwa, Jr. | |
| 6,558,324 B1 * | 5/2003 | Von Behren et al. | 600/440 |
| 7,303,530 B2 * | 12/2007 | Barnes et al. | 600/459 |
| 7,404,798 B2 * | 7/2008 | Kato et al. | 600/437 |
| 2002/0095087 A1 * | 7/2002 | Mourad et al. | 600/442 |
| 2005/0187473 A1 * | 8/2005 | Boctor et al. | 600/437 |
| 2010/0241000 A1 * | 9/2010 | Kondo | 600/454 |

FOREIGN PATENT DOCUMENTS

| | | |
|---|---|---|
| EP | 0 920 833 | 6/1999 |
| EP | 1 629 777 | 3/2006 |
| JP | 248102 | 9/2002 |
| JP | 2004-89362 | 3/2004 |

OTHER PUBLICATIONS

Naoyuki Murayama et al, "EUB-8500 ni okeru Real-Time Tissue Elastography Kino no Kaihatsu", Journal of Medical Ultrasonics, Apr. 15, 2004, vol. 31 Zokango, pp. S113.

* cited by examiner

*Primary Examiner* — Brian Casler
*Assistant Examiner* — Amanda Lauritzen
(74) *Attorney, Agent, or Firm* — Antonelli, Terry, Stout & Kraus, LLP.

(57) ABSTRACT

To carry out objective or definitive diagnosis on the basis of an elastic image regardless of experience and proficiency, a method of displaying an elastic image includes the steps of measuring ultrasound cross-section data of a cross-section region of a subject by applying pressuring to the subject, determining a physical value correlating with the elasticity of tissue in the cross-section region on the basis of the ultrasound cross-section data, generating an elastic image of the cross-section region on the basis of the physical value and displaying the elastic image on a display device, determine compression state information relating to the compression state of the cross-section region on the basis of the pressure applied to the subject, and displaying the compression state information together with the elastic image on the display device.

41 Claims, 23 Drawing Sheets

(A)

(B)

(C)

(A)

(B)

(A)

(B)

(A)

(B)

(C)

(A)

(B)

TIME AXIS DIRECTION t

REFERENCE DEFORMING BODY FIXING UNIT

REFERENCE DEFORMING BODY FIXING UNIT

PRESSURE MEASUREMENT UNIT

ULTRASOUND PROBE EQUIPPED WITH PRESSURE MEASUREMENT UNIT

METHOD OF DISPLAYING ELASTIC IMAGE AND DIAGNOSTIC ULTRASOUND SYSTEM

TECHNICAL FIELD

The present invention relates to a method of displaying an elastic image for displaying an elastic image representing the hardness or softness of body tissue in a region to be diagnosed by ultrasound diagnosis and relates to a diagnostic ultrasound system.

BACKGROUND ART

A diagnostic ultrasound system transmits an ultrasonic wave from an ultrasound transducer into a subject, receives a reflected echo signal, which is ultrasonic wave, corresponding to the structure of the body tissue from inside the subject, and displays a cross-sectional image, such as a B-mode image, for diagnosis.

Recently, it has been proposed to measure ultrasound image data by apply a compression force to a subject according to a manual or mechanical method, determining the displacement in regions of the body caused by the compression on the basis of two sets of ultrasound image data measured at different times, and generating an elastic image representing the hardness or softness of the body tissue on basis of displacement data of the regions of the body. Accordingly, pressure sensors are provided on the back of a transducer element unit of an ultrasound transducer, the pressure applied to the ultrasound transducer by compressing the subject is determined, and an elastic image is displayed after determining Young's modulus. When the pressure exceeds predetermined threshold value of pressure, a light-emitting diode provided on the probe is illuminated. Such a measurement method is described in Patent Document JP2003-225239A.

However, according to this patent document, only Young's modulus is calculated by determining the pressure applied to the ultrasound transducer, and there is no mentioning of displaying compression state information on a screen.

It has been reported that the hardness of body tissue is non-linear and that the hardness of body tissue changes depending on the compression condition at the time the body tissue is compressed (for example, Krouskop TA, et al. Elastic Moduli of Breast and Prostate Tissue Under Compression. Ultrasonic Imaging. 1998; 20:260-274). Here, the compression condition include the change over time in the pressure applied to body tissue, the change in the compressed amount (the compressed amount of body tissue from a non-compressed state), and the compression speed.

In other words, since the hardness of body tissue changes depending on the compression condition, the measured elastic image also changes depending on the compression condition. This will be described with reference to FIGS. 1(A) to 1(C). FIG. 1(A) shows an example image of when compression is adequate, where the region of hard tissue is represented by a black circle, and other regions of soft tissue are represented in white. FIG. 1(B) shows an example image of when compression is excessive, where distortion is generated in the black circle representing the region of hard tissue, the border of the black circle and the regions of soft tissue in the periphery is unclear, and the contrast of the image is reduced. FIG. 1(C) shows an example image of when compression is inadequate. Since sufficient stress is not applied to the body tissue, points of zero distortion (areas that are recognized as being hard) are scattered through out the region that is uniformly soft, and the image becomes non-uniform.

However, conventionally, it has been difficult for an examiner to objectively determine whether elastic information recognizable from an elastic image of a region of interest differed depending on the compression condition because there has not been any consideration given to detecting the compression condition and displaying information on the compression condition in association with the elastic image. As a result, since the examiner is forced to carry out a diagnosis on the basis of an elastic image measured under a compression condition (adequate compression, inadequate compression, or excessive compression) based on subjectivity, it is disadvantageous in that the diagnostic result differs depending on the examiner's experience and proficiency.

DISCLOSURE OF INVENTION

The present invention has taken into consideration the above problems, and its object is to enable objective or definitive diagnosis on the basis of an elastic image regardless of experience and proficiency.

To solve the above described problems, a method of displaying an elastic image according to a first aspect of the present invention includes the steps of measuring ultrasound cross-section data of a cross-section region of a subject by applying pressuring to the subject, determining a physical value correlating with the elasticity of tissue in the cross-section region on the basis of the ultrasound cross-section data, generating an elastic image of the cross-section region on the basis of the physical value and displaying the elastic image on a display device, determining compression state information relating to the compression state of the cross-section region on the basis of the pressure applied to the subject, and displaying the compression state information together with the elastic image on the display device.

Here, the physical value correlating with the elasticity is one of distortion and elasticity modulus of the tissue, and together with this, the elastic image may be one of the distortion image and the elasticity modulus image. The pressure applied to the subject may be applied with a compression member provided on the ultrasound transducer used in contact with the subject. The pressure in this case may be measured with either one of the pressure detecting means, i.e., a pressure sensor or a reference deforming body provided on the compression member. Instead, displacement of the tissue in the cross-section region may be determined on the basis of two sets of ultrasound cross-section data measured at different times, and the pressure applied to the subject may be determined on the basis of this displacement data.

In this way, with the method of displaying an elastic image according to the first aspect of the present invention, both the elastic image and the compression state can be simultaneously provided to the examiner. In other words, since the compression state information correlating to the pressure applied to the subject is displayed together with the elastic image, the examiner can determine the compression state (adequate compression, lack of compression, or excessive compression) on the basis of the compression state information displayed as an image and can carry out diagnosis based on the elastic image measured under adequate compression. As a result, objective or definitive diagnosis on the basis of an elastic image can be carried out regardless of experience and proficiency.

It is preferable to measure the elastic data by periodically changing the pressure applied to the subject. Therefore, the compression state information displayed on the display device changes in accordance with the change over time of the pressure applied to the subject.

The pressure applied to the subject may be applied through an ultrasound transducer used in contact with the subject. In this case, it is preferable that it is determined whether or not the pressure applied to the subject is within a set range on the basis of the compression state information and that at least one of audio and image representation is output as an alert when the pressure is not within the set range. In this way, the examiner can manually adjust the amount of compression applied through the ultrasound transducer and match the appropriate range. As an image representation, a graphic representation such as a downward arrow or an upward arrow may be used, colors such as blue when compression is adequate, red when compression is excessive, and yellow when compression is lacking may be used, or audio such as "decrease pressure" or "increase pressure" may be used.

In the above-described cases, the compression state information may be pressure distribution data determined in association with the long axis direction, which is the arrangement direction, of a plurality of transducers constituting the ultrasound transducer, and the pressure distribution data may be displayed on the display device as a line graph matching the coordinate direction corresponding to the long axis direction of the ultrasound transducer of the elastic image. In this case, the deviation with respect to the reference pressure of the pressure distribution data is determined, and the deviation is displayed on the display device as a line graph matching the coordinate direction corresponding to the long axis direction of the ultrasound transducer of the elastic image. In this way, the examiner can adjust the amount of compression in a uniform manner because it can be recognized that the amount of compression manually applied through the ultrasound transducer is biased.

Instead of displaying the compression state information as the pressure distribution, at least one set of an average value, a variance value, a median value, a maximum value, and a minimum value of a pressure distribution may be the pressure data of the pressure distribution, and the pressure data may be aligned on the elastic image and displayed on the display device. In this case, the pressure data may be at least one of a numerical value, a bar graph having a length corresponding the numerical value, a graphic representation having brightness or color corresponding to the numerical value, a bar graph having a length corresponding to the numerical value and having brightness or color corresponding to the numerical value, a simulation meter representing the numerical value with a rotational angle of a needle, a circular graphic representation having a diameter equaling the numerical value, and a graphic representation representing the numerical value by simulating a state of compression and deformation of the cross-section region. When a bar graph, a simulation meter, and a circular graphic representation are used for display, also the numerical scale of the pressure data may be displayed so that the amount of compression can be objectively recognized. Since the change in the compression state may be great, depending on the examined region, a logarithmic scale may be employed as the numerical scale. When displaying a graphic representation with brightness or color, a numerical scale for the pressure data may be displayed in association with the brightness or color.

A method of displaying an elastic image according to a second aspect of the present invention includes the steps of measuring ultrasound cross-section data of a cross-section region of a subject while repeatedly applying pressure to the subject, determining a physical value correlating with the elasticity of tissue in the cross-section region on the basis of the ultrasound cross-section data, generating an elastic image of the cross-section region on the basis of the physical value and displaying on a display device, determining the change over time in pressure applied to the cross-section region, and displaying a pressure change line graph together with the elastic image on the display device.

Accordingly, by looking at the pressure change line graph that is compression state information, it can be determined whether or not the maximum value and the minimum value of the pressure repeatedly applied to the subject and the frequency of the repeating cycle are suitable. The pressure change line graph in this case may be at least one set of pressure data of an average value, a variance value, a median value, a maximum value, and a minimum value of a pressure distribution determined in association with the long axis direction, which is the arrangement direction, of a plurality of transducers included in the ultrasound transducer. In particular, it is preferable to display a reference line graph on the display device in an overlapping manner on the pressure change line graph, which is an example of a change over time in pressure being applied to the cross-section region. In this way, the manual compression operation through the ultrasound transducer carried out by the examiner can be adjusted to an appropriate state.

When the pressure change line graph and the elastic image read out from the cine memory storing the pressure change line graph and the elastic image and when a mark is displayed on a time axis of the pressure change line graph and is moved along the time axis, an elastic image corresponding to the time indicated by the mark can be read out from the cine memory and displayed.

By freezing the pressure change line graph representing the change over time in the pressure and the elastic image, setting a start point and an end point of one cycle of the pressure change on the pressure change line graph, and storing the pressure change line graph and the elastic image corresponding to the set one cycle, an elastic image under an adequate compression condition may be repeatedly observed and definitive diagnosis becomes possible. In this case, the start point and end point of one cycle of pressure change may be automatically set.

A diagnostic ultrasound system that carries out the method of displaying an elastic image according to the present invention includes signal processing means for generating a cross-sectional image and an elastic image by processing a signal detected by an ultrasound transducer in contact with a subject, pressure detecting means for determining the pressure applied to the subject, compression state evaluation means for evaluating a compression state of the subject on the basis of pressure data determined by the pressure detecting means, and displaying means for displaying compression state information evaluated by the compression state evaluation means in association to the elastic image.

A cine memory for storing the pressure change line graph and the elastic image and control means for controlling the cine memory may be further provided, and the control means may displays a mark on a time axis of the pressure change line graph when the pressure change line graph and reads out an elastic image corresponding to the time indicated by the elastic image from the cine memory and displays the elastic image when the mark is moved along the time axis are stored in a cine memory. In this way, a pressure change line graph obtained by adequate compression operation may be objectively selected among those stored in the cine memory and may be used to carry out appropriate diagnosis.

In this case, the control means can freeze a pressure change line graph representing the change over time of the pressure and the elastic image, set a start point and an end point of one cycle of the pressure change on the pressure change line graph, and store the pressure change line graph and the elastic image corresponding to the set one cycle. In this way, an elastic image obtained by adequate compression operation may be arbitrarily selected among the elastic images stored in the cine memory while confirming information reflecting the change over time of the magnitude of the pressure data, and a range for the compression state optimal for diagnosis may be selected by the operation and stored.

The control means can automatically set the start point and end point of one cycle of pressure change. In this way, the beginning and the end of a period in which compression is carried out adequately, i.e., one cycle of adequate compression operation, can be automatically detected and selected, and the elastic image group for the one cycle can be stored and checked later.

BEST MODE FOR CARRYING OUT THE INVENTION

Figure 2:
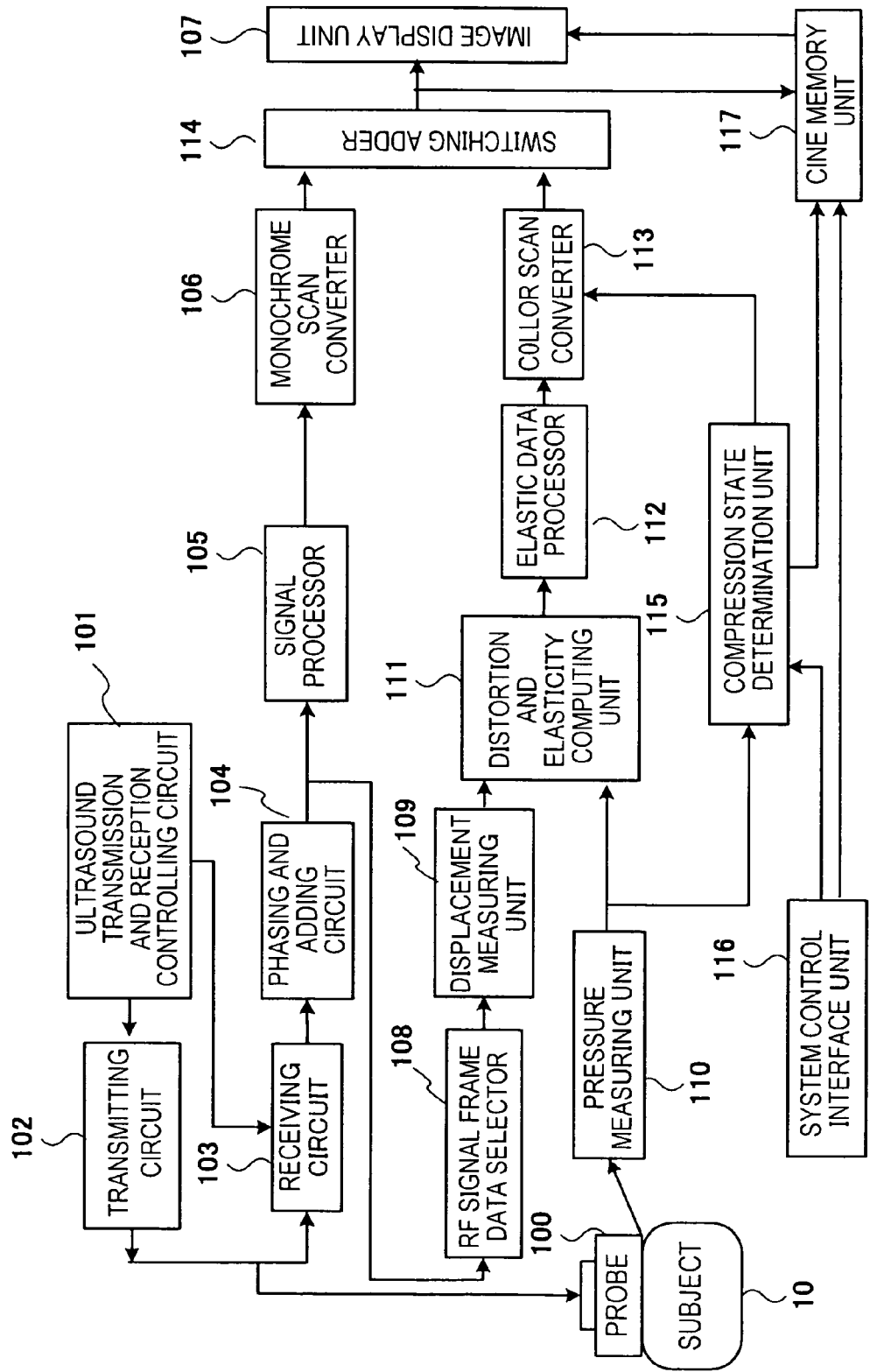
FIG. 2 is a block diagram illustrating a diagnostic ultrasound system according to an embodiment of the present invention.

Embodiments of the present invention will be described below in detail with reference to the accompanying drawings. FIG. 2 is a block diagram of a diagnostic ultrasound system according to an embodiment of the present invention. The diagnostic ultrasound system uses ultrasonic waves to obtain a cross-sectional image of a region to be diagnosed in a subject 10 and displays an elastic image representing the hardness or softness of body tissue of the subject 10. As shown in the drawing, the diagnostic ultrasound system includes a probe 100, an ultrasound transmission and reception controlling circuit 101, a transmitting circuit 102, a receiving circuit 103, a phasing and adding circuit 104, a signal processor 105, a monochrome scan converter 106, an image display unit 107, a system control interface unit 116, an RF signal frame data selector 108, a displacement measuring unit 109, a pressure measuring unit 110, a distortion and elasticity modulus computing unit 111, an elastic data processor 112, a color scan converter 113, a switching adder 114, a compression state evaluating unit 115, and a cine memory unit 117.

Figure 3:
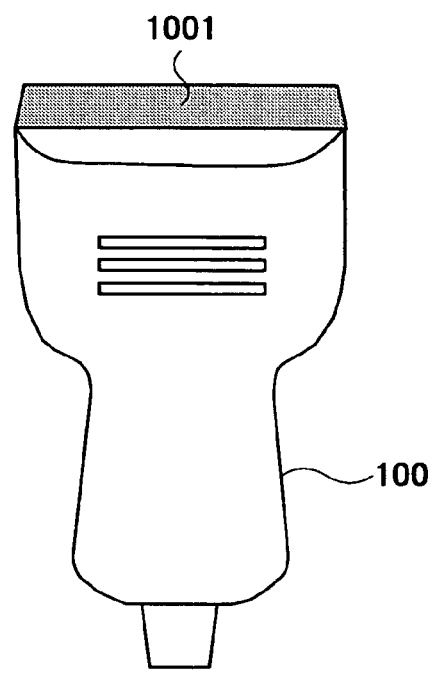
FIG. 3 illustrates an embodiment of an ultrasound transducer on which a compression plate is mounted.
Figure 3:
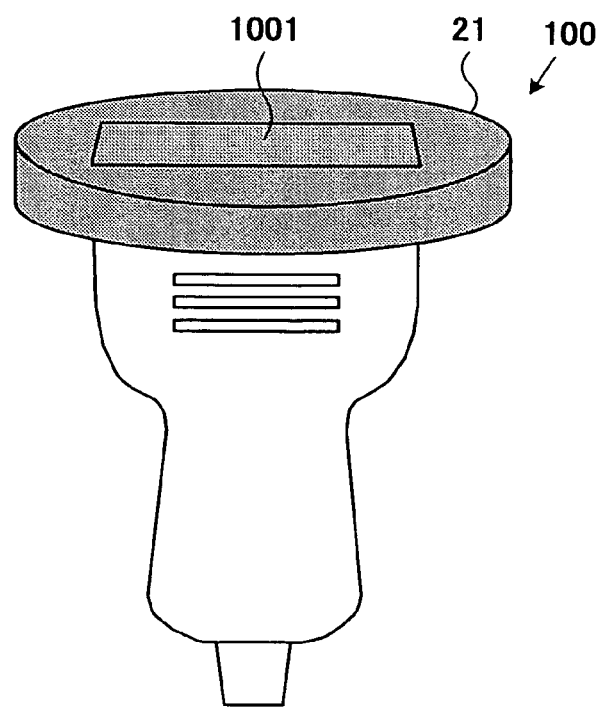

The probe 100 carries out mechanical or electrical beam scanning to transmit and receive ultrasonic waves to and from the subject 10. Element groups of a transducer that are the sources of ultrasonic waves and that receive reflected echo are aligned and disposed on the ultrasound transmission and reception surface of the probe 100. In general, the operation of compressing a subject to form an image of elasticity using ultrasound is carried out with an ultrasound transducer having a shape such as that shown in FIG. 3(A) or 3(B). In particular, with an object to effectively apply a stress distribution to the region to be diagnosed of the subject 10, an ultrasound transducer 100, such as that shown in FIG. 3(B), having a compression plate 21 attached flush with an ultrasound transmission and reception surface 1001 is used. Then, a method in which a compression surface constituted of both the ultrasound transmission and reception surface 1001 of the ultrasound transducer 100 and the compression plate 21 is contacted with the body surface of the subject 10 and the subject 10 is compressed by manually moving up and down the compression surface.

The ultrasound transmission and reception controlling circuit 101 controls the timing of transmitting and receiving ultrasonic waves. The transmitting circuit 102 drives the probe 100 to generate a transmission pulse for generating an ultrasonic wave. At this time, the convergent point of the transmitted ultrasonic wave is set to a predetermined depth by an embedded transmission delaying circuit. The receiving circuit 103 amplifies the reflected echo signal received by the probe 100 with a predetermined gain. The phasing and adding circuit 104 receives and controls the phase of the received signal amplified at the receiving circuit 103 and phases and adds the received signal from at least one convergent point. The signal processor 105 receives the received signal from the phasing and adding circuit 104 and carries out signal processing, such as gain correction, log compression, detection, edge enhancement, and filter processing. The probe 100, the transmitting circuit 102, the receiving circuit 103, the phasing and adding circuit 104, and the signal processor 105 as a whole constitute ultrasound transmission and reception means. By unidirectionally scanning an ultrasound beam along a cross-section region inside the body of the subject 10 using the probe 100, one cross-sectional image is obtained. The signal processor 105 constitutes signal processing means for generating a cross-sectional image.

The monochrome scan converter 106 includes an A/D converter for converting a reflected echo signal, which is ultrasound cross-sectional image data output from the signal processor 105, into a digital signal, a plurality of frame memories for time-sequentially storing the cross-sectional image data digitalized at the A/D converter, and a controller for controlling these operations. In other words, the monochrome scan converter 106 takes in the reflected echo signal output from the signal processor 105 and obtains RF signal frame data of the cross-section region at the ultrasonic wave cycle. The monochrome scan converter 106 includes cross-sectional scanning means for reading out RF signal frame data at television synchronization and controlling means for controlling the system.

The image display unit 107 is means for displaying the time-sequential cross-sectional image data obtained by the monochrome scan converter 106. More specifically, the image display unit 107 includes a D/A converter for taking in image data from the monochrome scan converter 106 via the switching adder 114 and converting the taken-in image data into an analog signal and a color television monitor for receiving the analog video signal input from the D/A converter to display an image.

The RF signal frame data selector 108 and the displacement measuring unit 109 diverge from the output side of the phasing and adding circuit 104. A pressure measuring unit 110 is provided in series with the RF signal frame data selector 108 and the displacement measuring unit 109. The distortion and elasticity modulus computing unit 111 is provided after the pressure measuring unit 110 and the displacement measuring unit 109. The output from the distortion and elasticity modulus computing unit 111 is input to the elastic data processor 112 to generate elastic image data. In other words, the distortion and elasticity modulus computing unit 111 and the elastic data processor 112 constitute signal processing means for generating an elastic image. The compression state evaluating unit 115 diverges from the output side of the pressure measuring unit 110. The elastic data processor 112 is provided after the distortion and elasticity modulus computing unit 111. The color scan converter 113 is provided after the elastic data processor 112. The switching adder 114 is provided at the output side of the compression state evaluating unit 115, the color scan converter 113, and the monochrome scan converter 106.

The RF signal frame data selector 108 stores, in order, the RF signal frame data sets that are time-sequentially output from the phasing and adding circuit 104 at a frame rate of the diagnostic ultrasound system in the frame memories in the RF signal frame data selector 108. The RF signal frame data currently stored in the RF signal frame data selector 108 is represented as RF signal frame data N. The sets of RF signal frame data stored before that is represented as RF signal frame data N-1, N-2, N-3, ... N-M. The RF signal frame data selector 108 selects one set of data from the RF signal frame data N-1, N-2, N-3, ... N-M in accordance with a control command from the diagnostic ultrasound system and outputs this data as RF signal frame data X to the displacement measuring unit 109 together with the RF signal frame data N. In other words, the RF signal frame data selector 108 outputs a pair of RF signal frame data (N, X). The output signal from the phasing and adding circuit 104 is referred to as RF signal frame data. Instead, however, this may be a signal having an I, Q signal format in which RF signals are combined and modulated.

The displacement measuring unit 109 measures the displacement or the displacement vector (direction and magnitude of displacement) of each measurement point on the cross-sectional image by carrying out one-dimensional or two-dimensional correlation processing on the pair of RF frame data selected at the RF signal frame data selector 108 and generates displacement frame data. As a method of detecting the displacement vector, for example, the block matching method or the gradient method described in JP5-317313A may be employed. According to the block matching method, an image is divided into, for example, blocks of N×N pixels, a block that is the most similar to the target block in the current frame is retrieved from the previous frame, and predictive coding is carried out by referring to the retrieved block.

Figure 4:
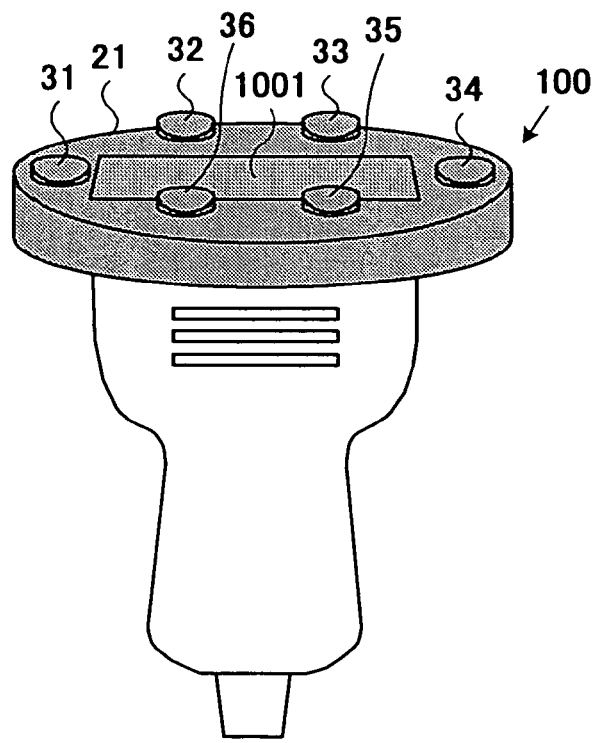
FIG. 4 illustrates an embodiment of an ultrasound transducer provided with pressure detecting means.
Figure 4:
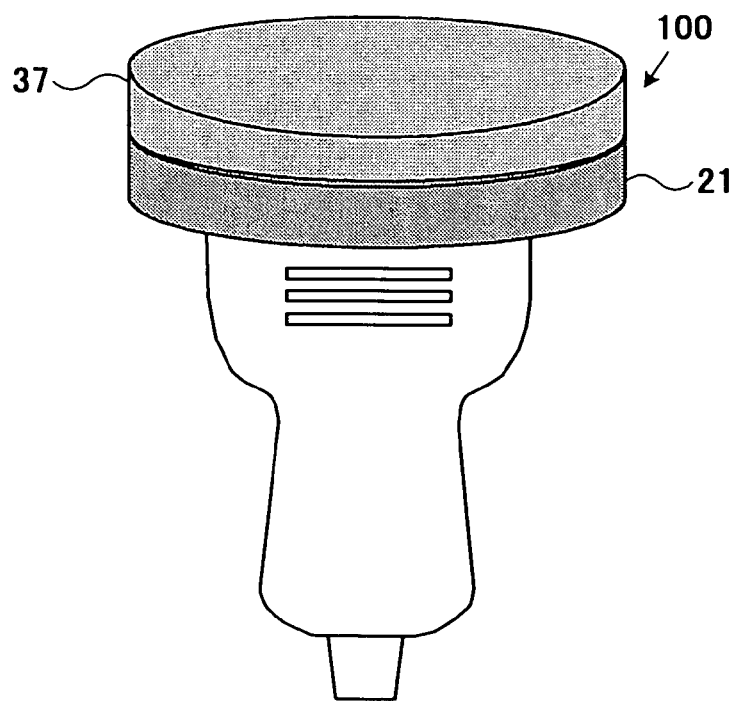

The pressure measuring unit 110 measures the pressure applied to the body surface of the subject 10 by using pressure sensors 31 to 36, such as those shown in FIG. 4(A), mounted on the compression plate 21 or a reference deforming body 37, such as that shown in FIG. 4(B), mounted on the compression plate 21. The measurement result is sent to the distortion and elasticity modulus computing unit 111 and the compression state evaluating unit 115 as pressure data. A method of obtaining the pressure data is described in detail in Japanese Patent Application Nos. 2003-178685 (JP2005-13283A) and 2003-300325 (JP2005-66041) that have been filed by the assignee of the present invention.

The distortion and elasticity modulus computing unit 111 computes the distortion and elasticity modulus at each measurement point on the cross-sectional image on the basis of the displacement frame data (amount of displacement) and pressure data obtained by the displacement measuring unit 109 and the pressure measuring unit 110, respectively, generates numerical data (elastic frame data) of the distortion or the elasticity modulus, and outputs it as elastic frame data to the elastic data processor 112. Distortion can be computed, for example, by carrying out spatial differentiation on the displacement, and pressure data is not required. For example, Young's modulus Ym, which is a value of the elasticity modulus, is computed by dividing stress (pressure) obtained at each computation point with the amount of distortion of each computation point, as represented by the following expression.

$$Ym_{i,j} = \text{stress(pressure)}_{i,j} / (\text{amount of distortion } i,j)$$

$$(i,j=1,2,3,\ldots)$$

where indices i,j represents the coordinates of the frame data.

The elastic data processor 112 carries out various types of image processing, such as smoothing and contrast optimization in the coordinate plane and smoothing between the frames in the time axis direction, on the elastic frame data input from the distortion and elasticity modulus computing unit 111 and sends the processed elastic frame data to the color scan converter 113. The elastic data processor 112 is described in detail in Japanese Patent Application No. 2003-006932 (JP2004-261198A) that has been filed by the assignee of the present invention.

The color scan converter 113 constitutes color information conversion means and receives the elastic frame data output from the elastic data processor 112 and the upper and lower limits of a gradation selection range included in a command from the diagnostic ultrasound system controlling unit or the elastic frame data from the elastic data processor 112. Then, color information, such as red, green, or blue, is added as elastic image data to the elastic frame data. For example, on the elastic frame data output from the elastic data processor 112, regions in which the measured distortion is great are converted into a red color code in the elastic image data, whereas regions in which the measured distortion is small are converted into a blue color code in the elastic image data.

The color scan converter 113 may be constituted of a monochrome scan converter so that region in which the measured distortion is great are displayed with high brightness, whereas a region in which the measured distortion is small are displayed with low brightness.

The switching adder 114 receives monochrome cross-sectional image data from the monochrome scan converter 106 and color elastic image data from the color scan converter 113, adds together or switches between both images, and outputs the result to the image display unit 107. In this case, switching can be carried out to output only the monochrome cross-sectional image data or only the color elastic image data or to output both sets of image data after adding and combining. In this case, as described, for example, in patent document JP2000-60853A, a monochrome cross-sectional image and a monochrome elastic image formed by the color or monochrome scan converter 106 may be simultaneously displayed on a two-screen display. Furthermore, for example, as described in patent document JP2004-135929A filed by the assignee of the present invention, a color elastic image may be translucently superimposed on the monochrome cross-sectional image. Then, display image data is output from the switching adder 114 to the cine memory unit 117 and the image display unit 107.

The compression state evaluating unit 115 according to this embodiment uses the pressure data output from the pressure measuring unit 110 to evaluate the current compression state of the region of interest and generates compression state information reflecting that compression state. The generated compression state information is formed into an image by the color scan converter 113 and is output to the image display unit 107 via the switching adder 114. In this way, an image of the current compression state information of the region of interest is displayed on the image display unit 107 so that a feedback can be provided to the examiner.

More specifically, according to the method of displaying an elastic image according to this embodiment, RF signal frame data, which is ultrasound cross-section data of a cross-section region of the subject, is measured while applying pressure to the subject with the ultrasound transducer 100, distortion or elasticity modulus, which are physical values, correlating to the elasticity of the tissue in the cross-section region is determined on the basis of the RF signal frame data, and an elastic image of the cross-section region that is generated on the basis of the distortion or the elasticity modulus is displayed on the image display unit 107. At the same time, compression state information related to the compression state of the cross-section region is obtained at the compression state evaluating unit 115 on the basis of the pressure applied to the subject 10, and this compression state information is displayed together with the elastic image on the image display unit 107.

Compression state information generated at the compression state evaluating unit 115 and embodiments of methods of displaying a compression state image and an elastic image will be described below.

First Embodiment

Figure 5:
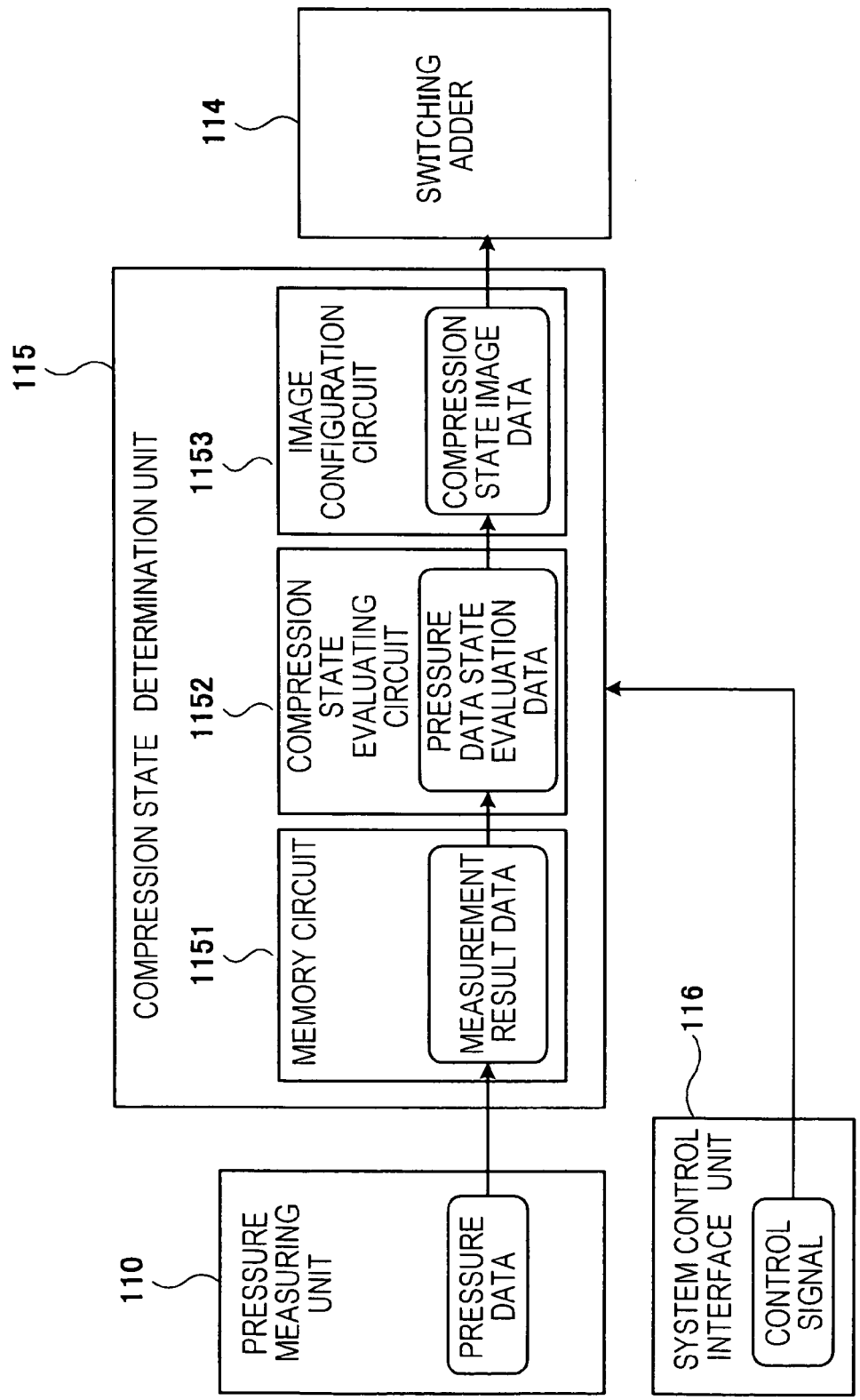
FIG. 5 is a block diagram illustrating an embodiment of a compression state evaluation unit which is a characteristic unit of the present invention.

FIG. 5 is a block diagram illustrating the flow of a process carried out by the compression state evaluating unit 115 according to this embodiment. The compression state evaluating unit 115 includes a memory circuit 1151, a compression state evaluating circuit 1152, and an image configuring circuit 1153. The memory circuit 1151 stores pressure data of the measurement result output from the pressure measuring unit 110 and outputs it to the compression state evaluating circuit 1152. The compression state evaluating circuit 1152 receives the pressure data output from memory circuit 1151, carries out statistical processing, such as overflow processing and average value calculation, on the pressure data so that an optimal image is displayed when displaying the compression state, and outputs numerical value data obtained as a result as compression state evaluation data to the following image configuring circuit 1153. The image configuring circuit 1153 receives the compression state evaluation data output from the compression state evaluating circuit 1152, configures an image reflecting the compression state evaluation data as compression state image data, and outputs it to the switching adder 114.

Figure 6:
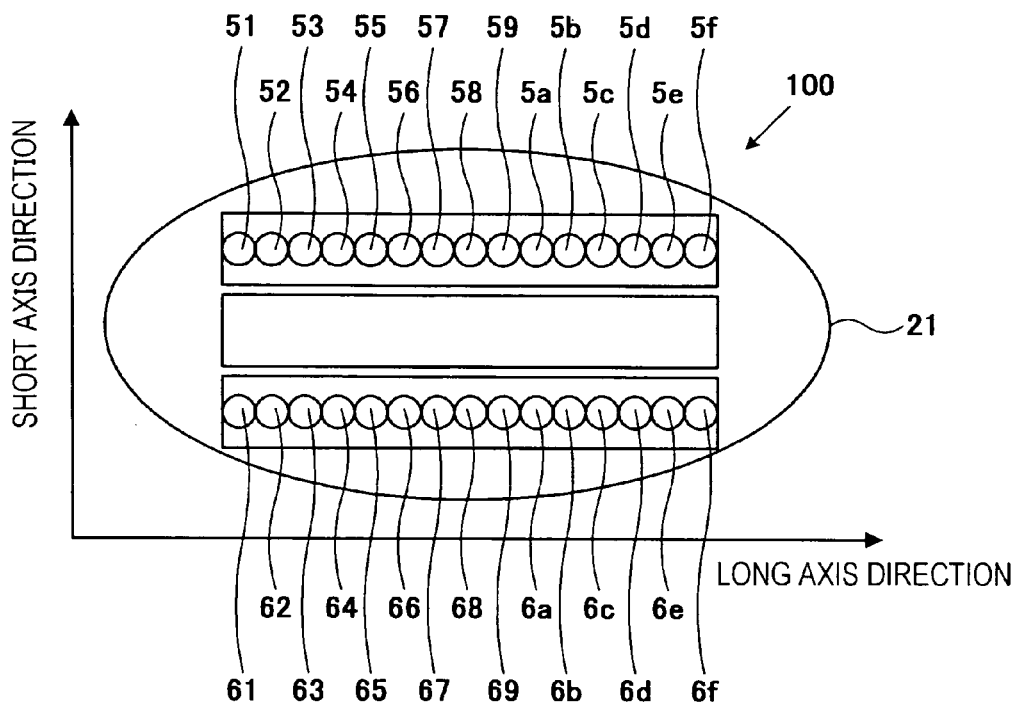
FIG. 6 illustrates a pressure sensor group including a plurality of pressure sensors disposed on a compression plate.

Next, an example of the operation of the compression state evaluating unit 115 will be described. A case in which pressure data measured using a plurality of sensors is displayed as a statistic characteristic will be described. FIG. 6 illustrates a modification of a probe used when pressure is measured using a plurality of sensors. In FIG. 4(A), the pressures sensors 31 to 36 are mounted along the periphery of the circular compression plate 21. For the probe in FIG. 6, a plurality of pressure sensor groups 5*l* to 5*f* and 6*l* to 6*f* of the pressure measuring unit are disposed on both sides of the compression plate 21 of the rectangular ultrasound transmission and reception surface 1001 along the long axis direction. A case in which compression state information is generated using the pressure data group from the pressure sensor groups 5*l* to 5*f* and 6*l* to 6*f* will be described.

The pressure data group output at time t from the pressure sensor groups 5*l* to 5*f* and 6*l* to 6*f* is represented as:

$$P_{i,j}(t)$$

$$(i=1,2,3\ldots,N; j=1,2,3\ldots,M)$$

where index i represents the coordinate in the long axis direction of the ultrasound transmission and reception surface of the probe and index j represents the coordinate in the short axis direction. All pressure data groups are referred to by the indices. The pressure data group $P_{i,j}(t)$ is stored in the memory circuit 1151 as a measurement result data group represented as:

$$R_{i,j}(t)$$

$$(i=1,2,3\ldots,N; j=1,2,3\ldots,M)$$

The compression state evaluating circuit 1152, for example, carries out statistical processing in which the measurement result data group $R_{i,j}(t)$ is a general population. The average value $<R_{i,j}(t)>$ is computed as a statistic characteristic value according to the following expression.

$$<R_{i,j}(t)> = \{\Sigma(\text{measurement result data } R_{i,j}(t))\}/(N \times M)$$

where the average value $<R_{i,j}(t)>$ is set as the compression state evaluation data.

Figure 7:
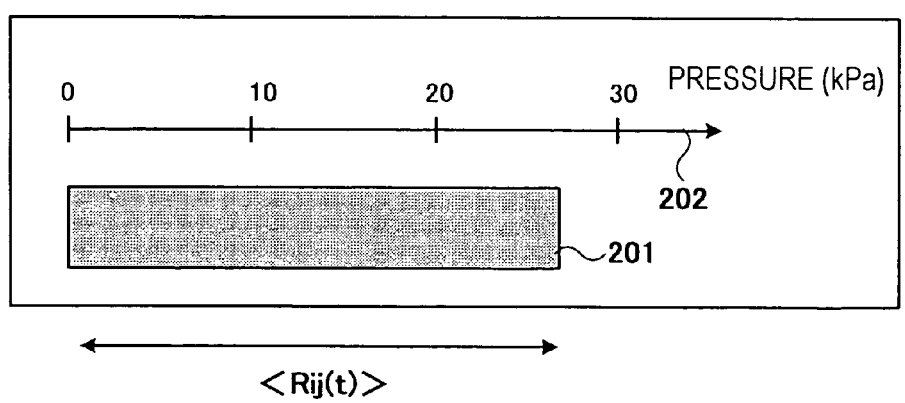
FIG. 7 illustrates compression state information formed into an image of a bar graph.

The image configuring circuit 1153 configures, for example, compression state image data for displaying an image of a bar graph 201 having a length corresponding to the average value $<R_{i,j}(t)>$ of the measurement result data group, as shown in FIG. 7. Furthermore, compression state image data for displaying an image of a gauge 202 with numerical values and a unit for the average value is configured.

The compression state image data changes over time depending on the current compression state. For example, as shown in a schematic view in FIG. 8, the lengths of bar graphs 203 representing the current compression state image data corresponding to the compression strength applied to target tissue 204 change over time.

Figure 9:
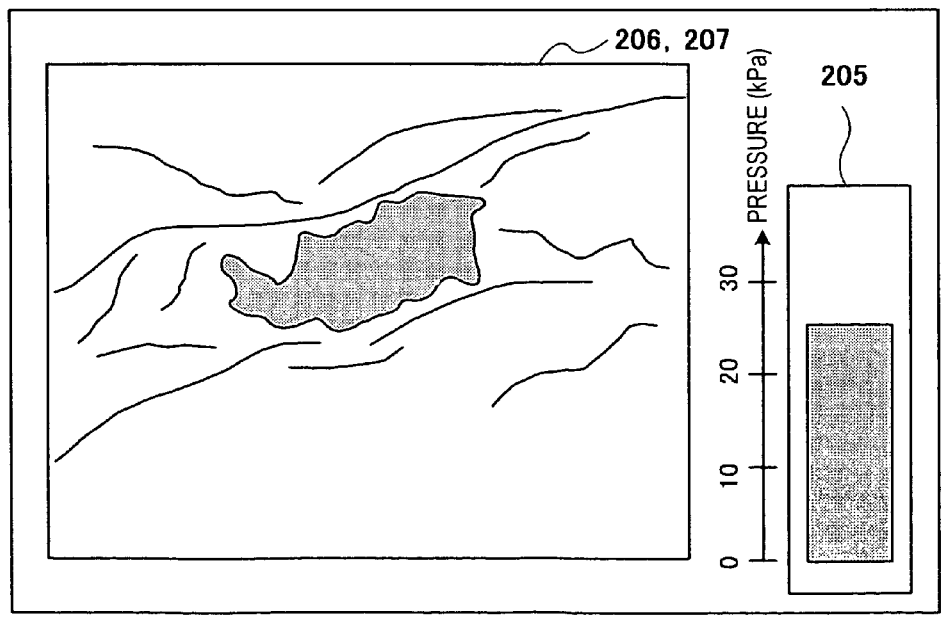
FIG. 9 illustrates an example of a displayed image in which compression state information represented as a bar graph image and an elastic image are simultaneously displayed.

FIG. 9 illustrates an example operation of the switching adder 114 according to this embodiment. When compression state image data is configured as described above and is output to the switching adder 114, one set of display image data, such as that shown in FIG. 9, is configured by combining a compression state image 205 that is output from the compression state evaluating unit 115, an elastic image 206 that is output from the color scan converter 113, and a cross-sectional image 207 that is output from the monochrome scan converter 106, and this display image data is sent to the image display unit 107 to allow observation by the examiner.

In the above-described embodiment, an example in which pressure sensors, such as those shown in FIG. 4(A), are used for the pressure measuring unit 110 is described. However, the present invention is not limited, and, for example, the reference deforming body 37, such as that shown in FIG. 4(B), may be used as a replacement of the pressure sensors to achieve the same operation. In other words, the reference deforming body 37 is provided in such a manner that the ultrasound transmission and reception surface 1001 of the ultrasound transducer 10 is covered, and then, the pressure applied to the body surface when the region to be diagnosed is compressed is measured by signal processing. Element groups of the transducer that are the sources of ultrasonic waves and that receive the reflected echo are aligned and disposed on the ultrasound transmission and reception surface 1001 of the ultrasound transducer 10. The border line of the reference deforming body 37 and the subject is represented by the distribution of pressure displayed on the image display unit 107.

A border detecting circuit (not shown in the drawings) uses RF signal frame data to detect the border of the skin of the subject 10 and the reference deforming body 37 and outputs the coordinates of the detected border of the RF signal frame data as border coordinate data to a pressure computing circuit (not shown in the drawings). The pressure computing circuit uses the border coordinate data detected by the border detecting circuit to extract an RF signal from the reference deforming body 37 from the RF signal frame data and determines the pressure applied to the border of the skin of the subject 1 and the reference deforming body 37 by computation. Since the elasticity modulus of the reference deforming body 37 is known, when this is Ym (for example, Young's modulus), the following relationship holds:

$$\text{pressure(stress)} pi = Ym \times (\text{amount of distortion } \delta di)$$

$$(i=1, 2, 3 \ldots n) \quad (1)$$

In this way, the pressure distribution inside data regions d1, d2, d3 ..., dn can be determined as pressure distributions p1, p2, p3 ... pn, respectively. By analyzing these pressure distributions pd1, pd2, pd3 ... pdn, the pressures at the border of the skin of the subject 10 and the reference deforming body 37 and directly and vertically below the transducers v1, v2, v3 ... vn can be determined as pressures p1, p2, 3 ... pn.

For the reference deforming body 37, it is preferable to use a material includes substances such as acoustic coupling material and acoustic lens material having excellent acoustic coupling characteristic with a living body and, at the same time, having excellent shape-reconstruction ability and shape-retaining ability such that substances have a small ultrasonic damping effect and such that the acoustic velocity and acoustic impedance are similar to those inside a living body. Normally, an acoustic coupling material is a material used to constitute an acoustic medium generally used in ultrasonographic diagnosis. The acoustic medium prevents the formation of a gap when the ultrasound transmission and reception surface 1001 of the ultrasound transducer 10 comes into contact with an uneven region, such as the surface of a living body. More specifically, when a gap forms between the ultrasound transmission and reception surface 1001 and the surface of a living body, an ultrasonic wave emitted from the ultrasound transducer 10 is reflected at the border of the air in the gap and the ultrasound transducer 10, causing problems in the displayed image. Such a problem is solved by providing an acoustic medium that transmits ultrasonic waves on the contact surface of the head unit of the ultrasound transducer 10 and the living body.

The reference deforming body may be constructed of an oil based gel material, a water based gel material, such as acrylamide, or a silicon based material. When the reference deforming body is constructed of a material having low viscosity, such as acrylamide, it is suitable for pressure measurement since it quickly responds to compression operation.

By using such a reference deforming body, the pressure directly below the transducer can be measured, and the pressure corresponding to an image can be measured. Moreover, pressure information can be obtained without using pressure sensors and a signal processing system.

As shown in FIGS. 32 to 35, a reference deforming body fixing unit is used to mount the reference deforming body to the transducer. The reference deforming body 37 and the fixing unit constitute one pressure measuring unit. The pressure measuring unit can be attached to and detached from the probe in a one-touch operation.

Figure 32:
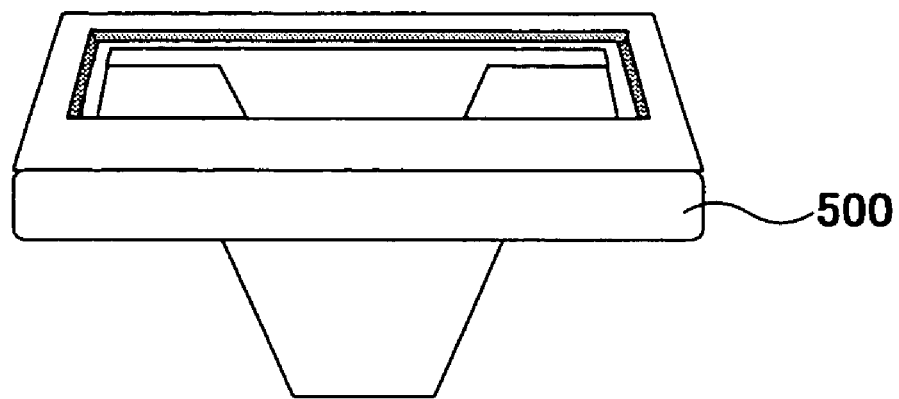
FIG. 32 illustrates a fixing unit for a reference deforming body and a fixing method.
Figure 32:
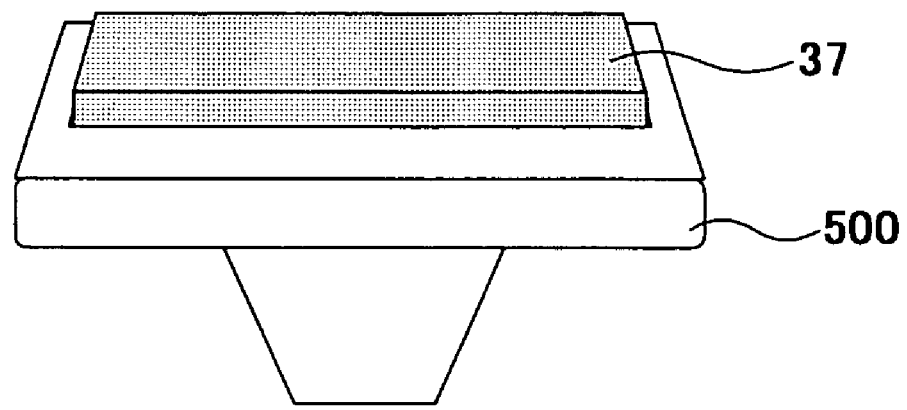

FIG. 32 illustrates the details of a fixing unit 500. The reference deforming body 37 is fixed to the inner frame of the fixing unit 500 by a method such as bonding or welding. The reference deforming body 37 instead may be fit into the inner frame of the fixing unit 500 so that the reference deforming body 37 can be attached and detached. The fixing unit 500 is provided with a protrusion (not shown in the drawing) that is fit into a groove on a side of the probe 100, and can be engaged in a one-touch operation. A depression (not shown in the drawing) is provided on the fixing unit 500 so that a protrusion provided on a conventional probe for recognizing the ultrasonic scanning direction can be grasped. The fixing unit 500 is provided with a non-slip grip (not shown in the drawing) to be grasped with a hand. The examiner holds the non-slip grip with their hand to compress the subject 10. To make it easy to hold the non-slip grip, the shape of the non-slip grip corresponds to the shape of fingers.

Figure 33:
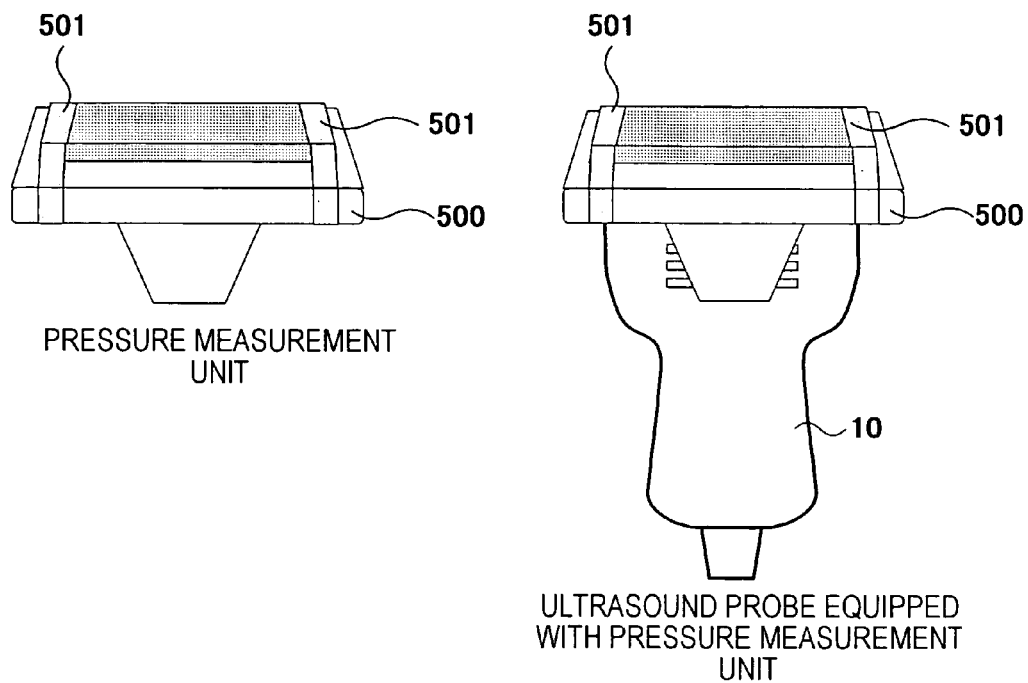
FIG. 33 illustrates another fixing method for a reference deforming body.

FIG. 33 illustrates an example in which the reference deforming body 37 is fixed to the fixing unit 500 with, for example, thin belts 501. In this way, both ends of the reference deforming body 37 are fixed by passing-two belts 501 around the fixing unit 500. The belts 501 are removable by adhesive tapes. The fixing unit 500 may be provided with a bag (not shown in the drawing) that transmits ultrasonic waves, and the reference deforming body 37 may be put into and taken out from the bag. Furthermore, the bag may have a window where ultrasonic waves pass through so that the ultrasound transmission and reception signals are not blocked by the bag.

As another method of fixing the reference deforming body 37, for example, a mechanism for moving in and out a needle may be provided on a groove wall of the fixing unit 500 so that the reference deforming body 37 is fixed by inserting a needle into the reference deforming body 37 after the reference deforming body 37 is fixed to the groove.

As the above-described pressure measuring unit, a reference deforming body that is suitable for measuring the target tissue can be selected from various reference deforming bodies having different shapes, harnesses, and acoustic characteristics and can be combined with the fixing unit 500. For example, when the entire target tissue is relatively hard or when the affected region in interest is deep, pressure can be effectively applied to the target tissue by using a hard reference deforming body, and a high-quality elastic image can be easily obtained.

Figure 34:
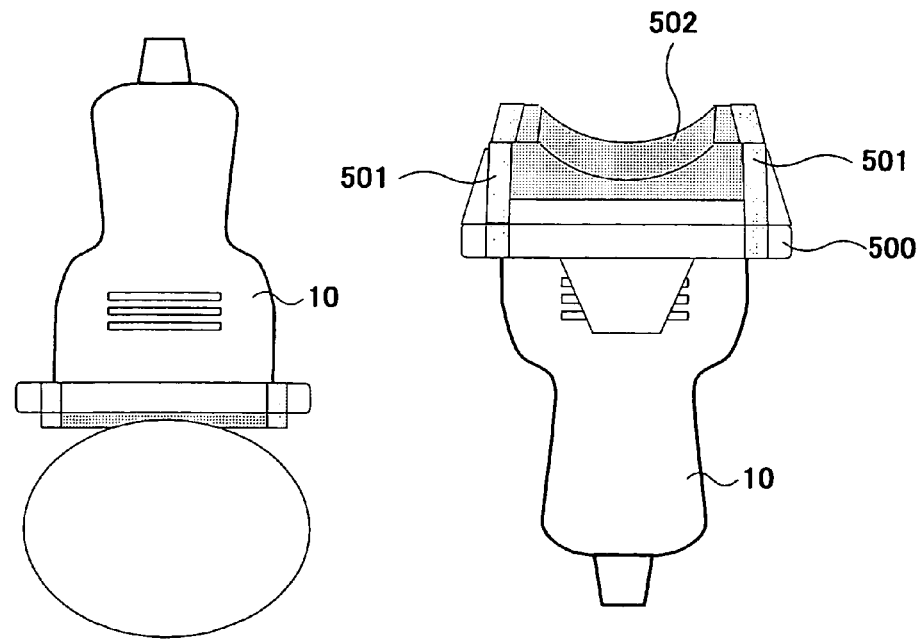
FIG. 34 illustrates an example of a concave reference deforming body.

When the pressure measuring unit is used for evaluating the thyroid gland, it is difficult to apply uniform pressure from the skin since the neck is convex-shaped, as shown in FIG. 34.

Thus, by using a convex reference deforming body 507 that reflects the convex shape of the neck, a pressure measuring unit capable of applying uniform pressure to the skin of a living body can be provided.

Figure 35:
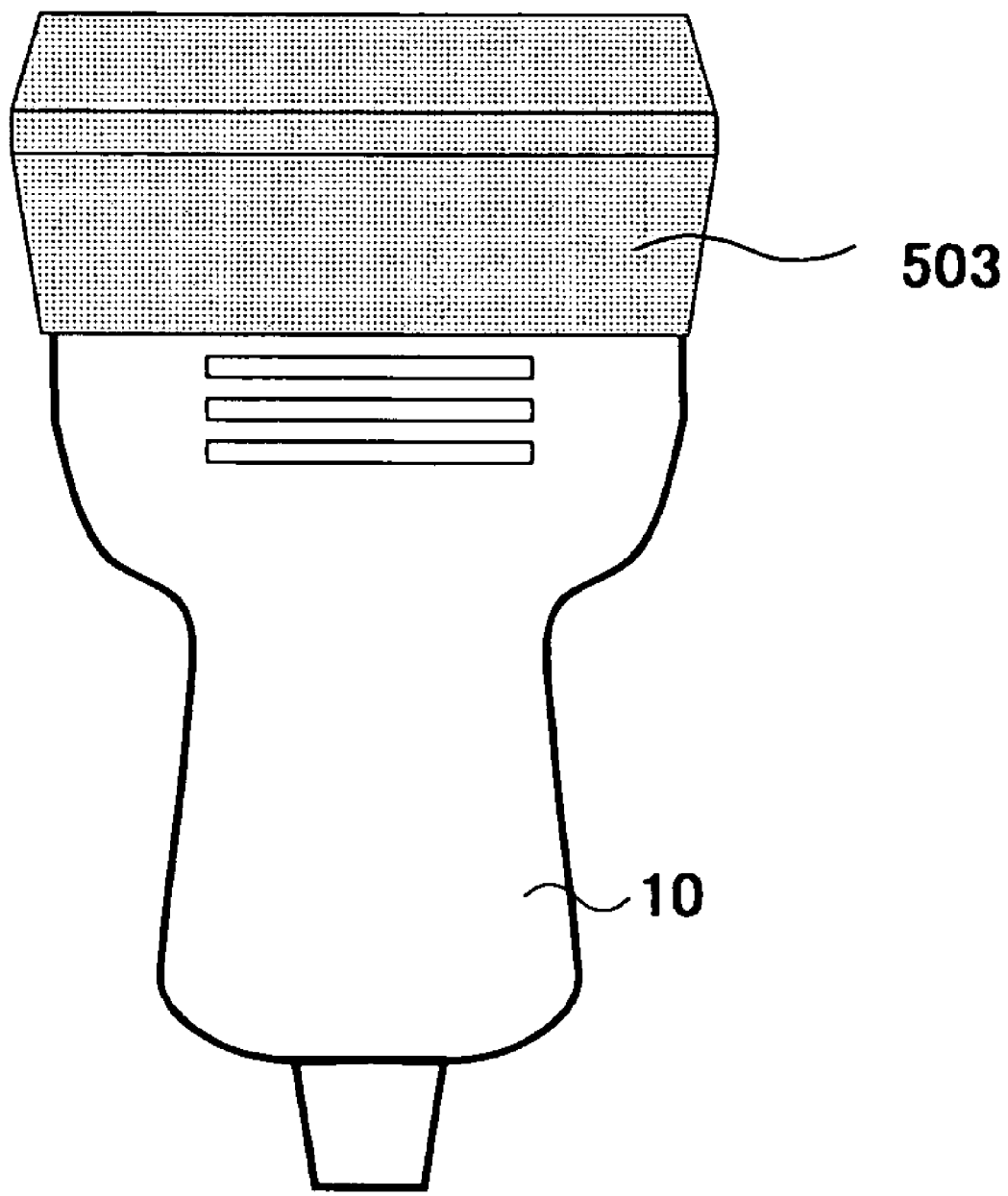
FIG. 35 is an external view of an example of a reference deforming body and a fixing unit formed as a single unit.

In the above, an example in which a pressure measuring unit is constituted by combining a reference deforming body and a reference deforming body fixing unit is described. However, the present invention is not limited, and the reference deforming body and the reference deforming body fixing unit may be provided as an integrated unit (for example, the entire unit being made of silicon), as shown in FIG. 35, and, for example, the integrated unit may be formed into a cap that can be easily attached by covering the probe.

In the above-described embodiment, an example in which a plurality of pressure sensors is used in the pressure measuring unit 110, as shown in FIG. 4(A), is described. However, the present invention is not limited, and only one pressure sensor may be attached to the compression plate provided on the pressure measuring unit 110 so that compression state image data is configured at the compression state evaluating unit 115 in accordance with the magnitude of the pressure data output from this pressure sensor.

In the above-described embodiment, a case in which a pressure data group output from the plurality of pressure sensors used in the compression state evaluating unit 115 to compute the average value by statistical processing and display a compression state image is described. However, the present invention is not limited, and a variance value, a median value, a maximum value, or a minimum value based on statistics on a general population that is the pressure data group may be used, and compression state information representing a statistic characteristic of the pressure data group may be displayed. Moreover, not only one statistic characteristic may be displayed, but, instead, a plurality of statistic information items may be simultaneously displayed.

Second Embodiment

Figure 10:
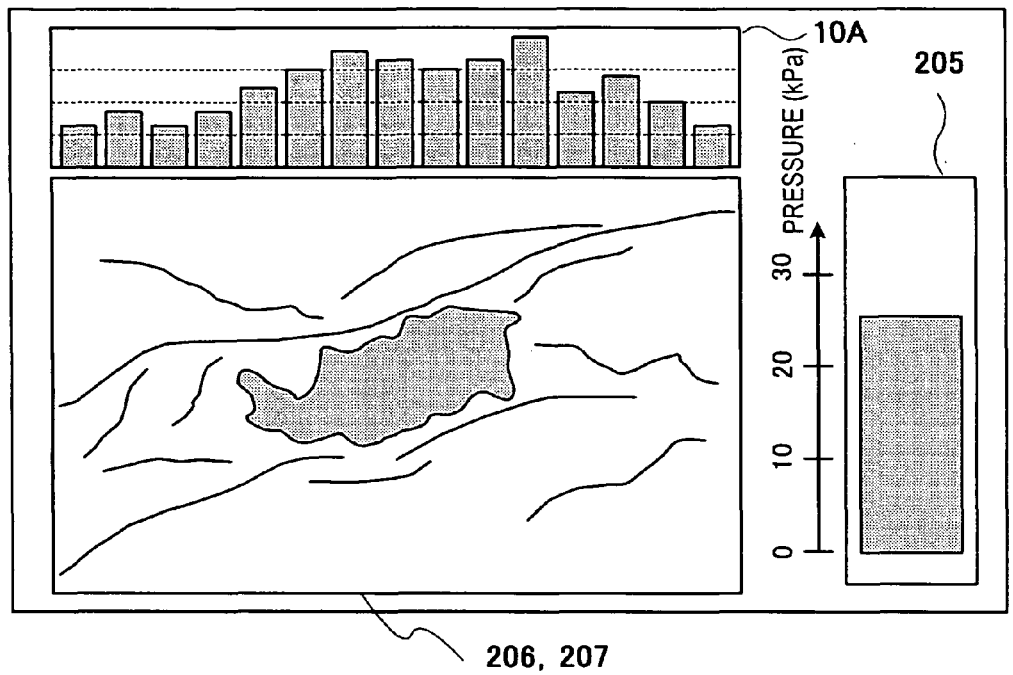
FIG. 10 illustrates an example in which pressure distribution in a long axis direction of an ultrasound transducer is displayed in association with an elastic image.

In the first embodiment, a case in which a pressure data group output from a plurality of pressure sensors in the pressure measuring unit 110 is used to display a statistic characteristic as compression state information is described. However, the present invention is not limited, and sets of pressure data of the pressure sensors may be used to configure sets of compression state image data, and each set of compression state image data may be displayed independently. In other words, when a plurality of pressure sensors is disposed along the long axis direction of the ultrasound transmission and reception surface, as shown in FIG. 6, the positions of the pressure sensors and the corresponding positions in the elastic image and the cross-sectional image may be matched, and each set of compression state image data 10A that is configured independently for each set of the pressure data may be displayed, for example, as shown in FIG. 10. In FIG. 10, the heights of the bar graphs of the sets of compression state image data 10A correspond to the pressure sensors 5*l* to 5*f* and 6*l* and 6*f* in FIG. 6. Since two sensors of the pressure sensors 5*l* to 5*f* and 6*l* and 6*f*, shown in FIG. 6, are disposed in the short axis direction, the average value of the two pressures sensors in the short axis direction and the height of the graph of the compression state image data 10A in FIG. 10 correspond to each other. Therefore, by visually confirming the compression state image data 10A in FIG. 10, the examiner can accurately grasp the state of compression in the long axis direction of the probe.

More specifically, as shown in FIG. 10, the pressure distribution determined in association with the long axis direction, which is the alignment direction of the plurality of transducers included in the ultrasound transducer, is represented as bar graphs matching the coordinate direction of the elastic image corresponding to the long axis direction of the ultrasound transducer. Instead of the bar graphs in the compression state image data 10A, a line graph may be displayed.

Third Embodiment

Figure 8:
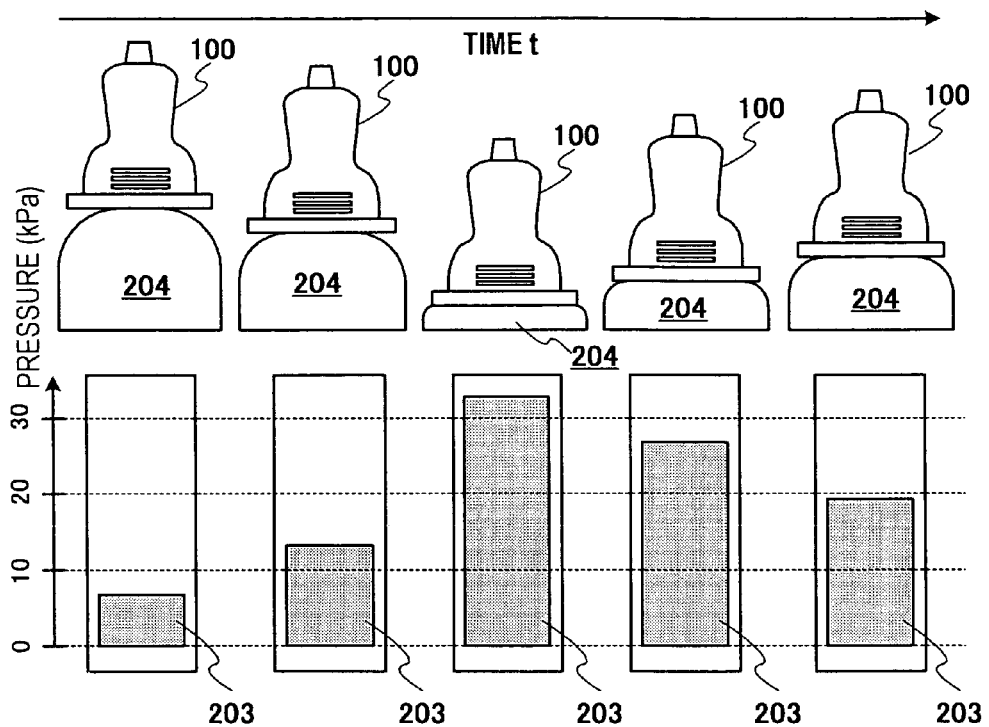
FIG. 8 illustrates that the length of a bar graph representing current compression state information changes in accordance with the strength of compression.
Figure 11:
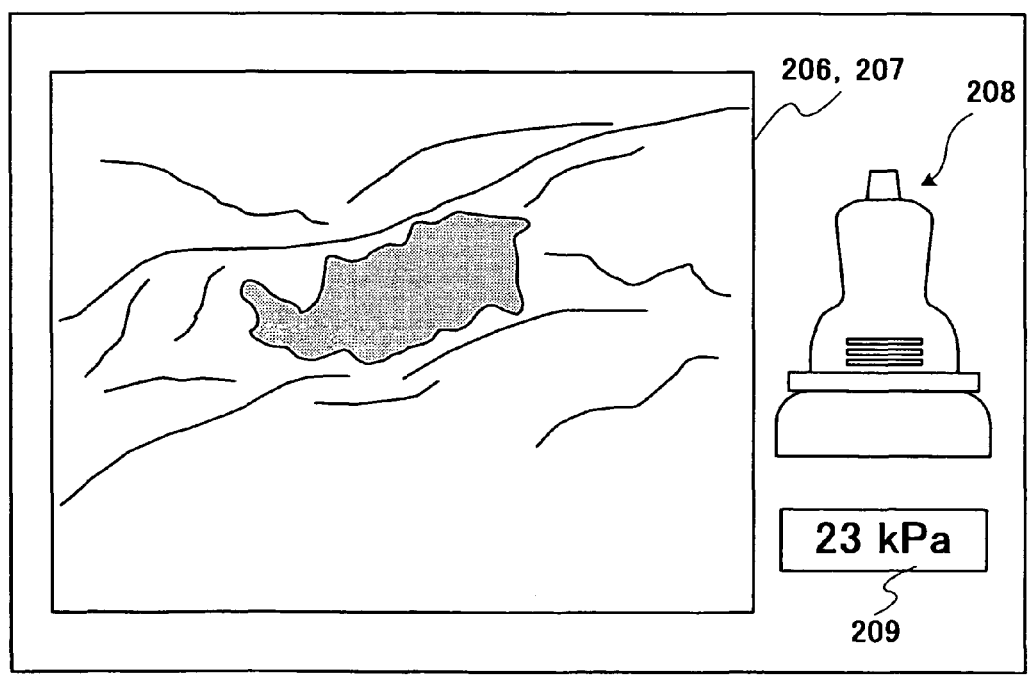
FIG. 11 illustrates an example in which compression state information is represented as a graphic representation simulating the state of compression and deformation of a subject.

FIG. 11 illustrates an example in which the bar graphs in the displayed image in FIG. 9 is replace with a graphic representation 208 simulating the state of compression and deformation of the cross-section region being compressed by the probe shown in the upper section of FIG. 8. By displaying the state of the target tissue being compressed by the probe, the examiner can intuitively recognize the compression state. In FIG. 11, a pressure data value 209 is displayed at the lower area of the schematic diagram of the probe and the target tissue.

Fourth Embodiment

Figure 12:
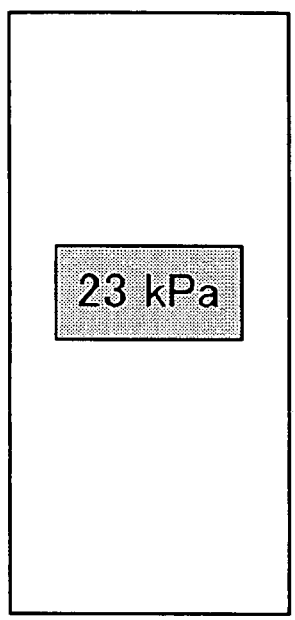
FIG. 12 illustrates examples of various methods of displaying pressure data of compression state information.
Figure 12:
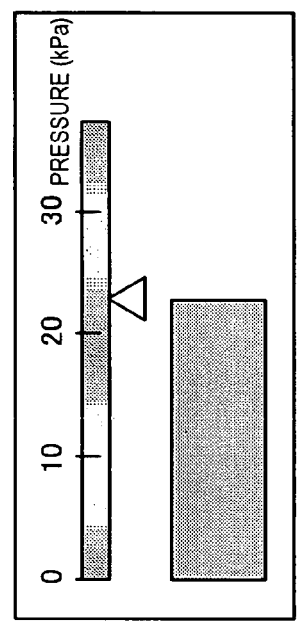
Figure 12:
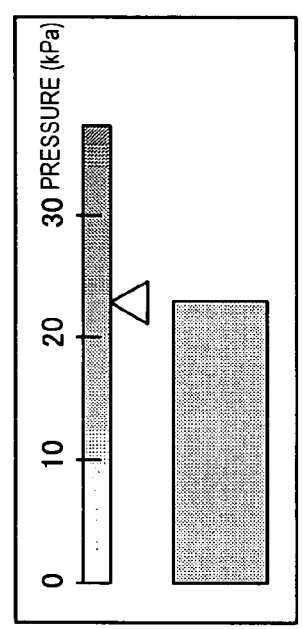

In the first embodiment, a case in which the compression state evaluating unit 115 configures compression state information, or, in particular, compression state image data for displaying bar graphs, is described. However, the present invention is not limited, and any method may be employed so long as information reflecting the magnitude of the pressure data is displayed. For example, as shown in FIG. 12(A), the pressure data may be directly displayed as numerical data on the order of pressure. Furthermore, as shown in FIG. 12(B), the pressure data may be converted into color information and displayed in colors. Moreover, as shown in FIG. 12(C), the pressure data may be converted into brightness information and displayed in brightness. Accordingly, it is acceptable so long as the magnitude of the pressure data can be determined from the display.

Figure 13:
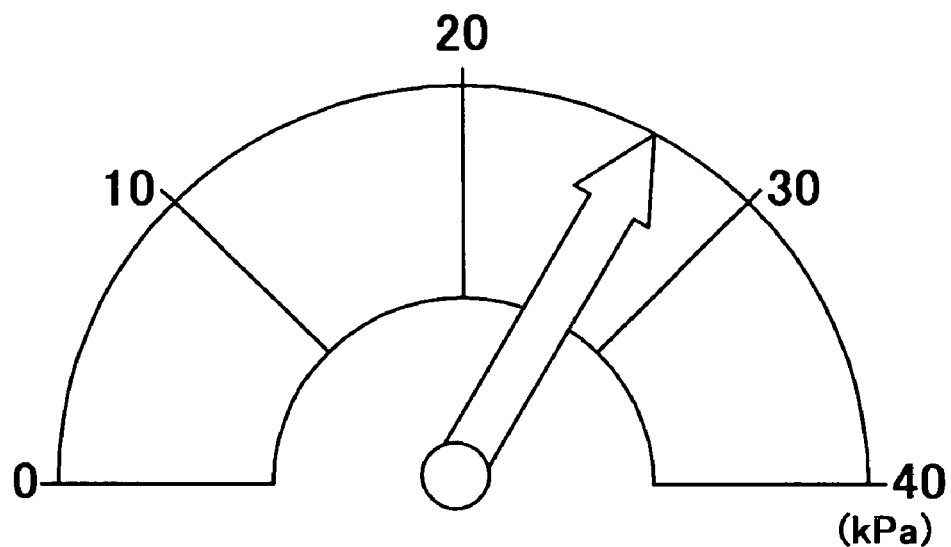
FIG. 13 illustrates a modification of a displayed image of compression state information.
Figure 13:
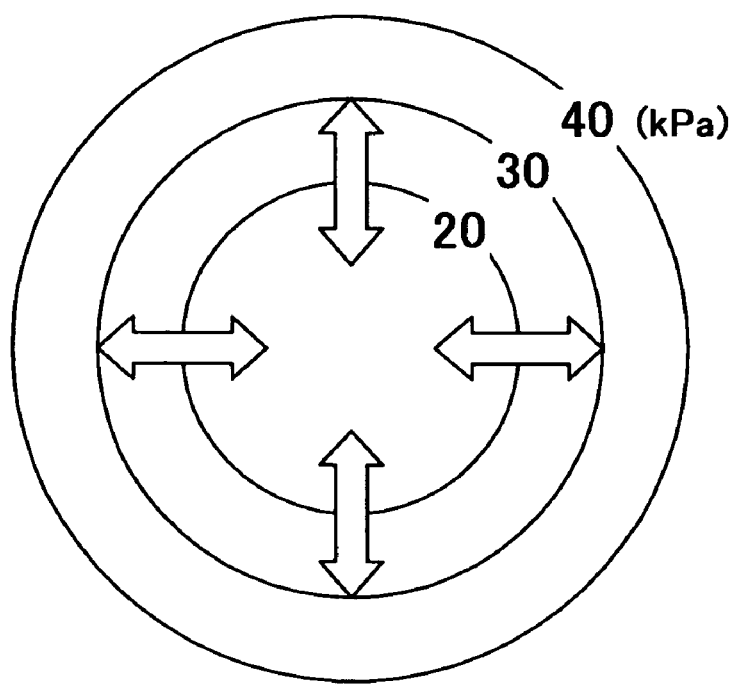

As shown in FIG. 13(A), the pressure data, which is compression state information, can be displayed in a meter system in which a rotary needle points at a semi-circular scale representing the pressure data. Moreover, as shown in FIG. 13(B), the pressure data, which is compression state information, can be displayed by the sizes of circles. Any other display method may be employed so long as the display method enables the compression state to be grasped instantaneously. The unit of the displayed pressure is not limited to [kPa] and may be any unit such as [mbar], [Torr], [arm], [kgf/cm$^3$], or [psi]. The setting can be switched on the side of the diagnostic ultrasound system. Moreover, the setting may be switched so that numerical values and the unit are not displayed.

When displaying the pressure data in colors or brightness, the visibility is improved compared to when displayed in numerical values. By providing a scale corresponding to the pressure data and displaying the magnitude of the pressure data on the scale, the magnitude of the pressure can be easily recognized.

Fifth Embodiment

Figure 14:
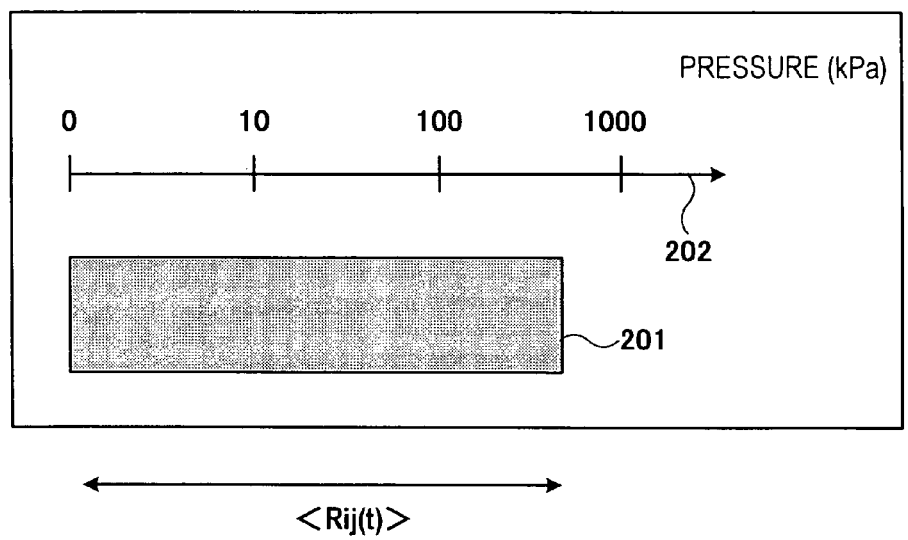
FIG. 14 illustrates a modification in which pressure data of compression state information is displayed using a bar graph.

FIG. 14 illustrates a modification of a case in which bar graphs are used as a compression state image representing compression state information. The first and other embodiments describe examples in which the gauge section is set by lines. However, in the case of FIG. 14, the scale of a gauge 202 is a logarithmic display. For the logarithmic display, a scale other than that is shown in the drawing may be used.

Sixth Embodiment

Figure 15:
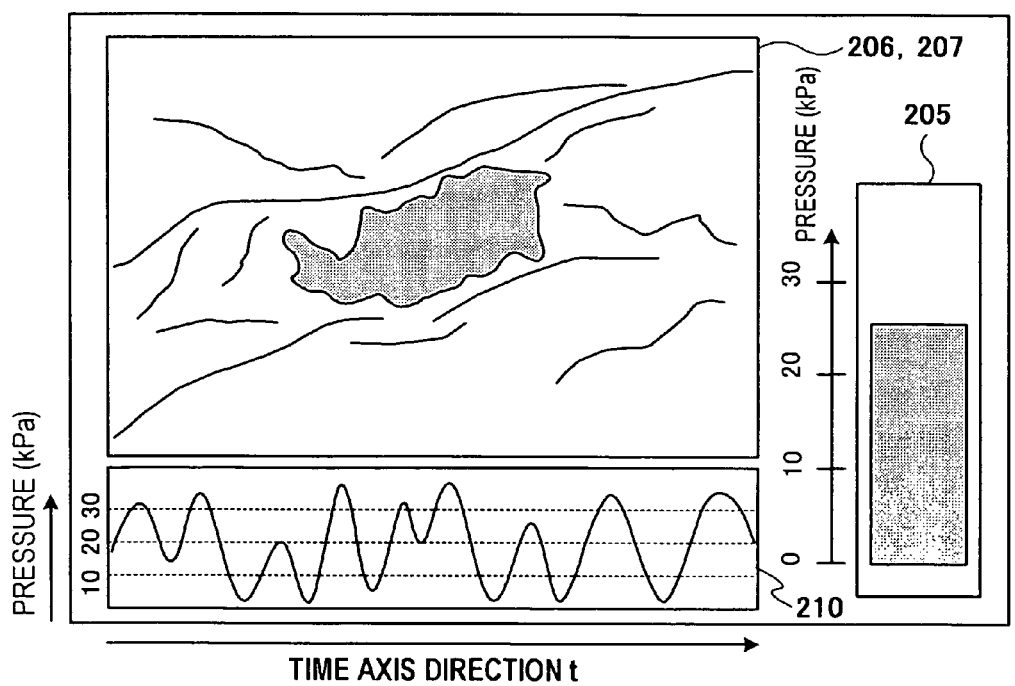
FIG. 15 illustrates an example in which a change over time, from the past to the present, in the pressure state is represented as a pressure change line graph.
Figure 16:
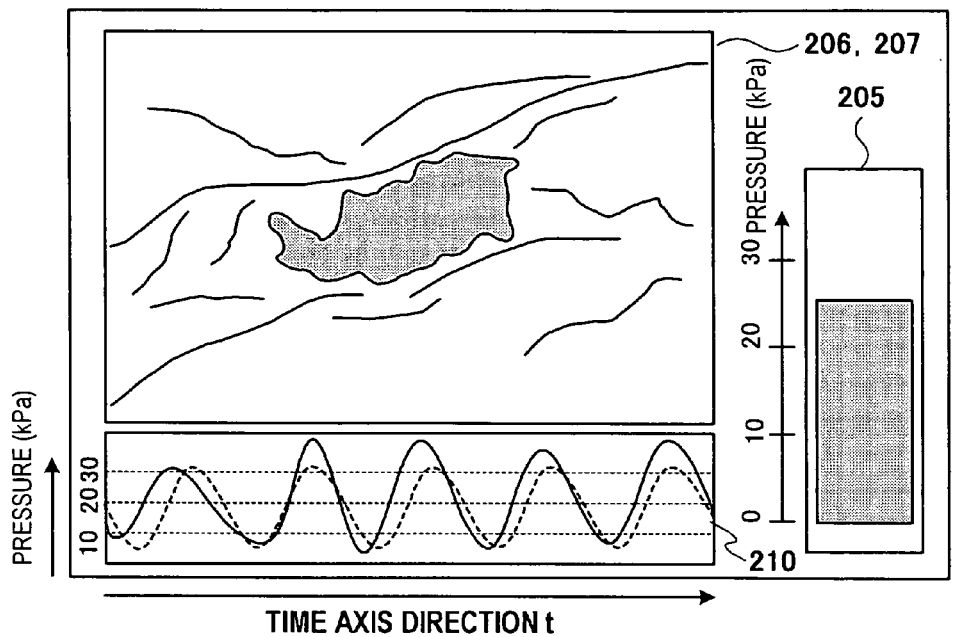
FIG. 16 illustrates an example in which an example of compression operation is displayed on the pressure change line graph of the compression state shown in FIG. 15.

FIG. 15 illustrates an example of a display method for representing the change over time of pressure, which is compression state information. In the above-described embodiments, a case in which a pressure change diagram 210 displaying information on the current compression state is configured at the compression state evaluating unit 115 is described. However, the present invention is not limited, and, for example, as shown in FIG. 15, compression state image data may be configured so that the change over time, from the past to the present, of the compression state can be observed and finally displayed on the image display unit 107, allowing observation by the examiner. For example, the graph may be displayed in a scrolling manner similar to that of an oscilloscope in which the change of voltage over time can be observed. The display method is not limited to a line graph, and any other display method may be employed so long as information reflecting the change over time in the magnitude of the pressure data is displayed. Furthermore, for example, as shown in FIG. 16, a curved line (the curved dotted line in the drawing) representing an example compression operation may be displayed in the compression state image data that represents the change over time of the compression state so that the curved line function as a guide that can be followed by the examiner to carry out compression.

Seventh Embodiment

Figure 17:
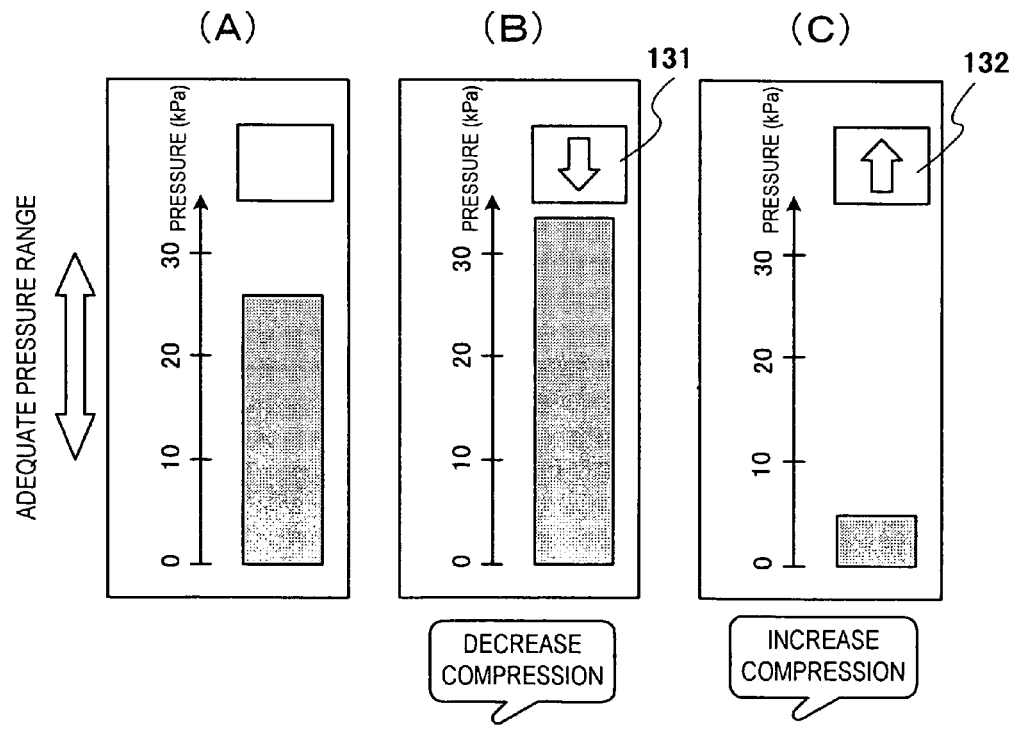
FIG. 17 illustrates an example in which inadequate compression is detected and provided as feedback to the examiner.

FIG. 17 illustrates an example of a case in which feedback (warning) is provided to indicate that the compression state is inadequate. In the above-described embodiments, a case in which pressure state image data is configured at the compression state evaluating unit 115 using pressure data output from the pressure sensors so that the compression state information is displayed as graphs is described. However, the present invention is not limited, and the compression state evaluating unit 115 may have a function for detecting an inadequate current compression state, such as excessive compression or lack of compression, of the compression operation during elastic image diagnosis on the basis of the pressure data. In such a case, for example, a downward arrow 131 or an upward arrow 132 may be displayed as feedback information alerting the examiner to decrease the compression if the compression is excessive, such as shown in FIG. 17(B), or to increase the compression if the compression is lacking, such as shown in FIG. 17(C). In FIG. 17, the pressure range of 10 to 20 kPa is set as an adequate compression range. If the pressure is greater, compression is excessive and if the pressure is smaller, compression is lacking. This adequate compression range is an example and is not limited. The compression range can be set appropriately and modified. In particular, the method of providing feedback to the examiner is not limited to an image, and, for example, as shown in the drawing, the same object may be achieved by an audio voice, such as "decrease pressure" or "increase pressure." The object of this is not only to indicate an excessive, dangerous state but is to instruct an adequate compression method for obtaining a high-quality image.

In other words, according to this embodiment, it is determined whether or not the compression force is within a set range, and when the compression force is not within the set range, at least one of audio and an image display is output as an alert.

Eighth Embodiment

Figure 18:
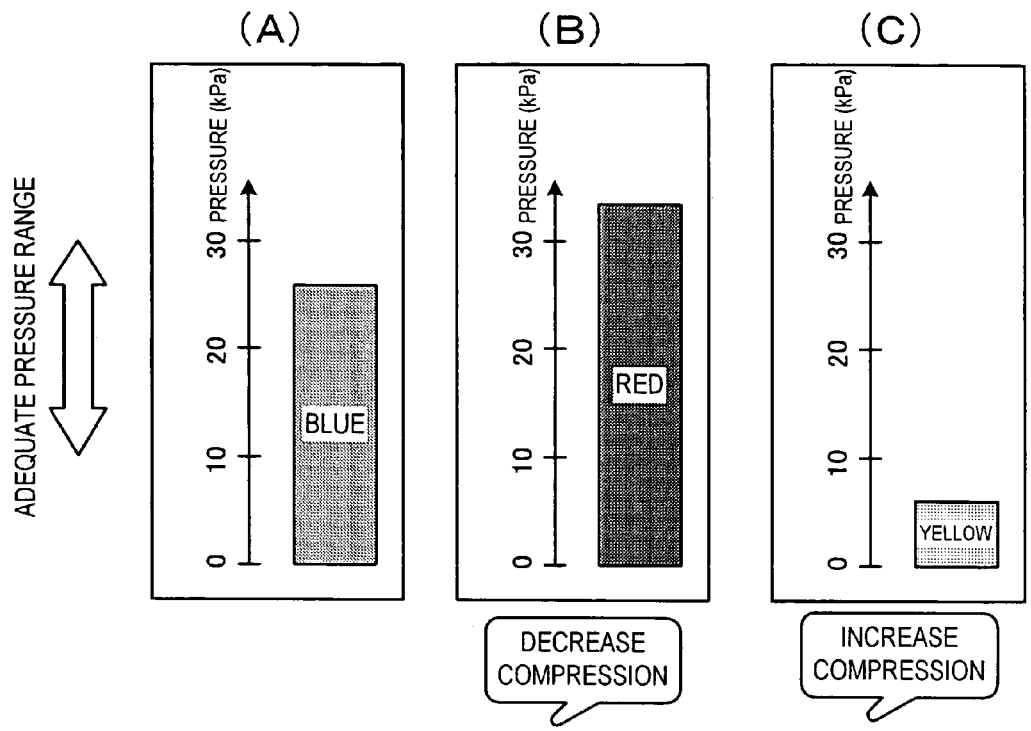
FIG. 18 illustrates another example in which the pressure range is within an adequate compression range.

FIG. 18 illustrates a modification of a display for a case in which the pressure range is within an adequate compression range. In FIG. 17, the pressure range of about 10 to 20 kPa is set as an adequate compression range. If the pressure is greater, compression is excessive and if the pressure is smaller, compression is lacking, and the downward arrow 131 or the upward arrow 132 is displayed. In FIG. 18, the color of a bar graph may be changed to blue (FIG. 18(A)) when compression is adequate, to red (FIG. 18(B)) when compression is excessive, and to yellow (FIG. 18(C)) when compression is lacking so as to represent the compression range by colors. When representing by colors, the color may be gradually changed. Furthermore, the color of a graphic representation imitating the state of compression and deformation of a cross-section region compressed by a probe, such as that shown in the upper section of FIG. 8, may be blue when compression is adequate, red when compression is excessive, and yellow when compression is lacking. In this way, the compression state can be recognized just by looking at a glance.

According to the first to eighth embodiments as described above, the current compression state of, for example, a region of interest can be evaluated by the compression state determination unit 115 and image information reflecting the compression state can be generated and displayed on the image display unit 107 in association with an elastic image. As a result, the compression state can be provided as feedback to the examiner, and the examiner can objectively evaluate the compression state of the displayed elastic image at any time. At the same time, a predetermined unique compression state can be generated and reconstructed. In this way, a constant compression state determined to be employed for the diagnosis can be realized, an elastic image obtained under the predetermined compression conditions can be selected, and accurate image diagnosis can be carried out. Furthermore, at the same time, a situation in which different examiners draw different diagnostic results due to image diagnosis carried out under a compression condition depending on the subjectivity of the examiners can be prevented. Thus, objective and universal diagnosis is established, and a diagnostic ultrasound system that is clinically useful is provided.

Ninth Embodiment

A cine memory unit 117 according to a conventional method has functions for storing display image data in a memory, retrieving display image data of the past in accordance with a control signal from the system control interface unit 116 for display on the image display unit 107, and transmitting the selected display image data on a recording medium, such as an MO, for recording. In contrast, the cine memory unit 117 according to this embodiment has a function for referring to and extracting elastic image data by using information of the compression state image data section in the display image data chronologically stored in a memory provided inside the cine memory unit 117. Details of the cine memory unit 117 according to this embodiment will be described below in detail.

Figure 19:
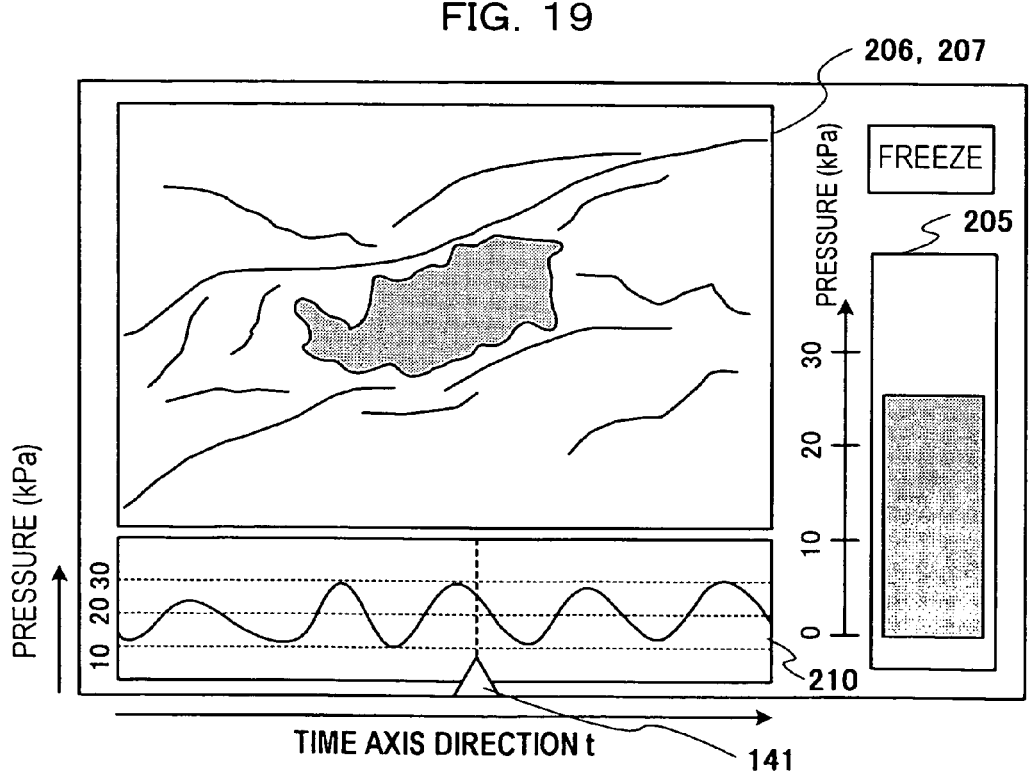
FIG. 19 illustrates an example in which a predetermined time is assigned on the pressure change line graph so that an elastic image corresponding to the time is displayed in conjunction.

FIG. 19 illustrates an example of an operation of the cine memory unit according to this embodiment. First, the examiner refers to the compression state image data of the image configuration circuit 1153 in the compression state determination unit 115 and display the display image data for the same time on the image display unit 107. For example, as shown in FIG. 19, the diagnostic ultrasound system is frozen by a control signal from the system control interface unit 116, and elastic image data included in the display image data stored in the cine memory unit 117 and assigned by a triangular button 141 on the image display unit 107 is displayed in order on the image display unit 107. The slide control of the button 141 is carried out by a mouse via the system control interface unit 116. When the time of a desired compression state is assigned by the button 141, elastic image data corresponding to the time is selected from the cine memory unit 117 and is displayed in order on the image display unit 107, as shown in FIG. 19.

Tenth Embodiment

Figure 20:
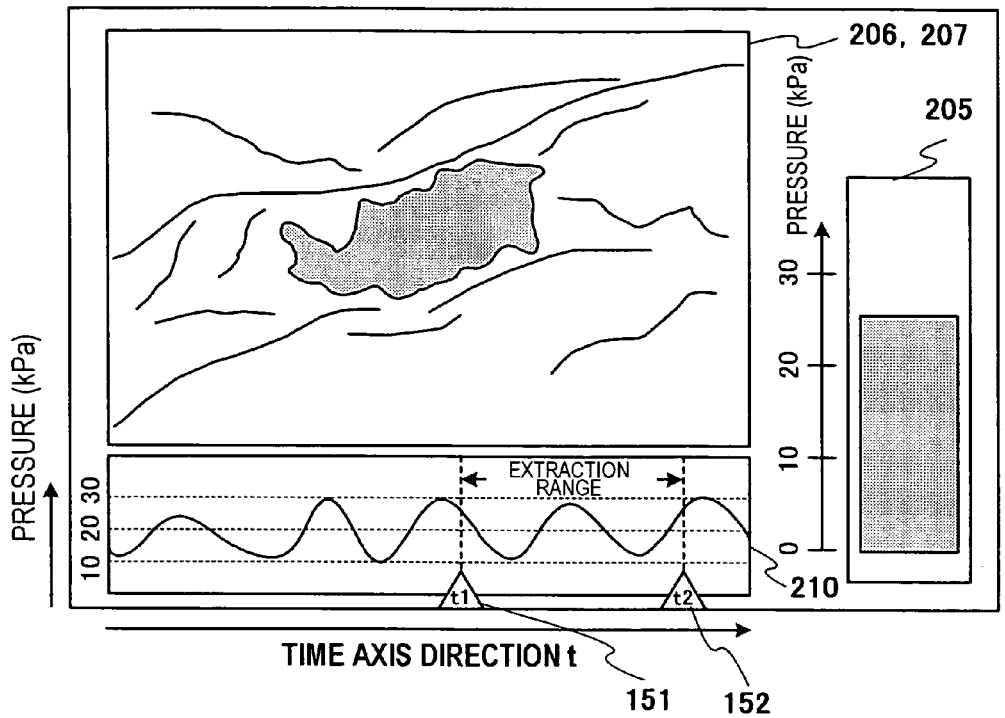
FIG. 20 illustrates an example in which two predetermined points of time are assigned on the pressure change line graph, and an elastic image group corresponding to the points of time is extracted.

FIG. 20 illustrates an example of a case when the examiner selects an optical compression state on the basis of a graph representing the compression state and stores the selected compression state. For example, as shown in FIG. 20, the diagnostic ultrasound system freezes by a control signal from the system control interface unit 116 and selectively displays display image data corresponding to a predetermined time that is stored in the cine memory unit 117 on the image display unit 107. Compression state image data representing the change over time of a compression state included in the display image data is displayed, as shown in FIG. 20, and the examiner assigns a frame for time t1 at the beginning of a period of adequate compression and a frame of time t2 at the end of the period of adequate compression by sliding triangular buttons 151 and 152. In this way, a display image data group (frame group) that time-sequentially exists in the period of time t1 to time t2 is extracted from the cine memory unit 117 and is stored.

Eleventh Embodiment

Figure 21:
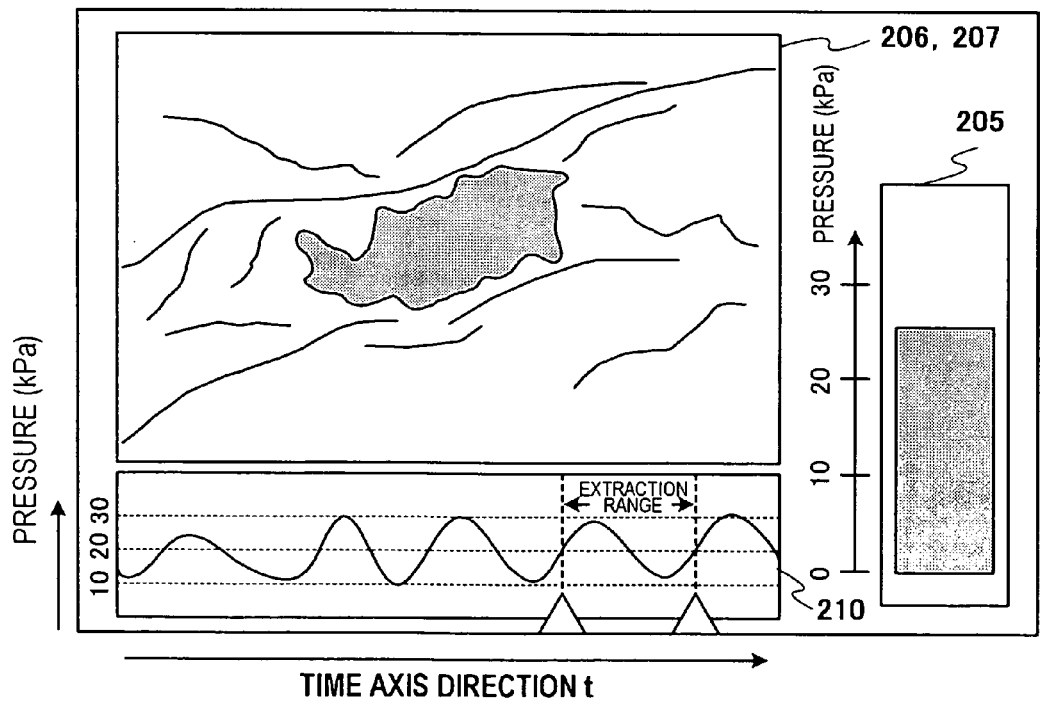
FIG. 21 illustrates an example in which one cycle of an adequate compression state is automatically detected, and the elastic image group of the one cycle is set as a storage range.

FIG. 21 illustrates an example of a case when one cycle in an adequate compression state is automatically detected and is set as a storage range. With reference to FIG. 20, a case in which the examiner refers to a compression state image to extract consecutive display image data for the assigned range from the cine memory unit 117 is described. Here, the beginning and end of a period of adequate compression is automatically detected (extracted). For example, as shown in FIG. 21, one cycle of adequate compression operation is automatically detected, and a display image data group of this cycle is stored.

With reference to FIG. 21, a case in which display image data obtained while the compression state is adequate is extracted from the cine memory unit 117 using information of the compression state image data unit. Instead, however, compression state evaluation data output from the compression state evaluating circuit 1152 of the compression state determination unit 115 may be used to achieve the same operation.

According to FIG. 21, the display image data group extracted from the cine memory unit 117 by determining a range is displayed on the image display unit 107 in accordance with a control signal from the system control interface unit 116. Instead, however, replay display of a continuously repeated loop or transferring to and recording on a recording medium, such as an MO, is also possible.

Twelfth Embodiment

Figure 22:
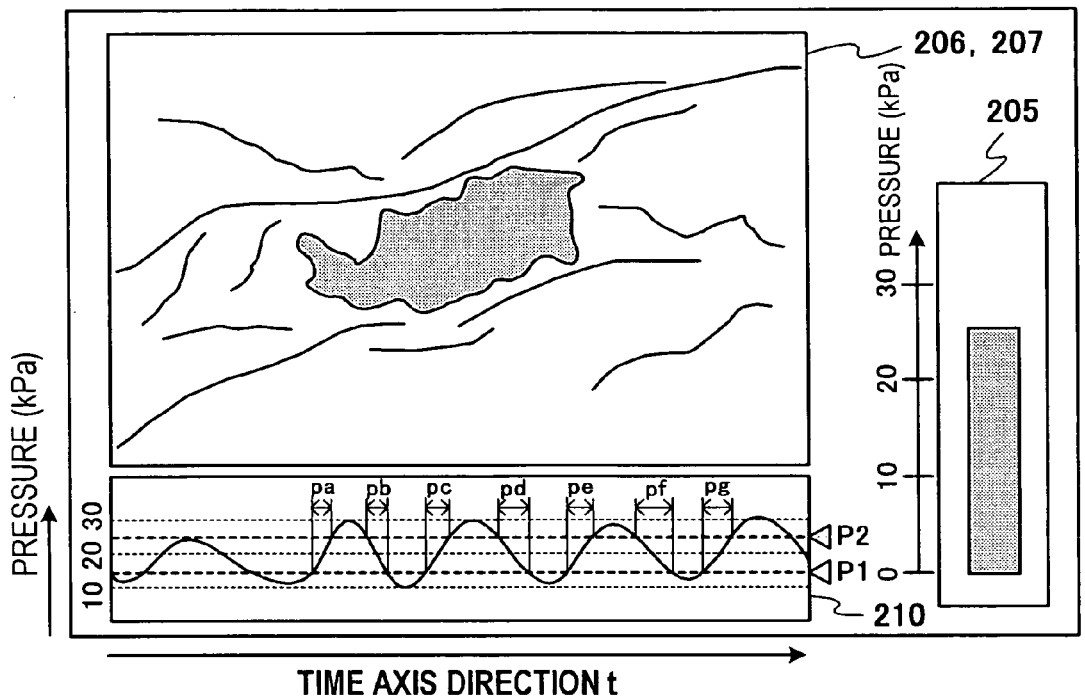
FIG. 22 illustrates an example in which a period of an adequate compression state is set within the pressure range, and the elastic image group within the range is set as a storage range.

FIG. 22 illustrates an example of a case in which the range of a period of an adequate compression state is set by the magnitude of the pressure axis and is set as a storage range.

With reference to FIG. 21, a case in which the beginning and end of a period of adequate compression is automatically detected (extracted) and is stored as a display image data group for one cycle is described. Here, sets of adequate compression data P1 and P2 are set in the pressure axis direction, and by passing through this range, a compression period pa to pg is extracted. This detection can be carried out automatically or manually.

Thirteenth Embodiment

Figure 23:
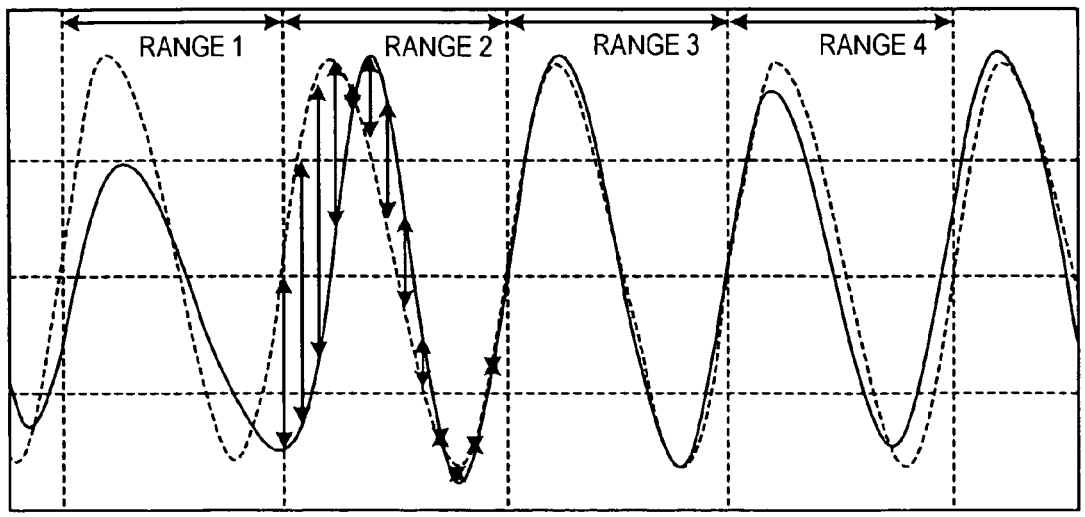
FIG. 23 illustrates an example of a detection method in which one cycle of an adequate compression state is automatically detected.

FIG. 23 illustrates an example of a detection method when an adequate cycle is automatically detected. First, from a curve of the actual compression state (the solid line in the drawing), ranges (range 1, range 2, . . . ) can be defined as shown in the drawing. Next, as shown in the drawing, at each sampling point, the difference of the curve of the actual compression state and a sample compression curve (dotted line in the drawing) is computed. In each range, the sum of the difference at each sampling point is computed, and the range with the smallest sum can be extracted as the optimal one cycle. In FIG. 23, the range 3 is selected as the optimal range. So long as a range that matches the best to the sample curve is extracted as an optimal cycle, any method, such as a least-square method or computation of the correlation coefficient, may be employed. The cycle is not limited to one cycle and, instead, half a cycle or a plurality of cycles may be extracted automatically at appropriate points.

According to this embodiment, the compression state determination unit 115, the switching adder 114, and the cine memory unit 117 are used to extract elastic images obtained under predetermined compression conditions on the basis of an objective criterion. Thus, definitive image diagnosis, not depending on subjectivity, can be efficiently carried out.

Fourteenth Embodiment

According to the above-described embodiments, the compression state determination unit 115, the switching adder 114, and the cine memory unit 117 are described on the basis of various information items representing the compression state and, in particular, data of an absolute pressure value output from a pressure sensor. Instead, however, for example, compression state image data may be generated using the change over time in the pressure data (pressure change in adjacent compression frames) and the current pressure change data (tilt of the pressure value) in the compression process and displayed on the image display unit 107.

Figure 25:
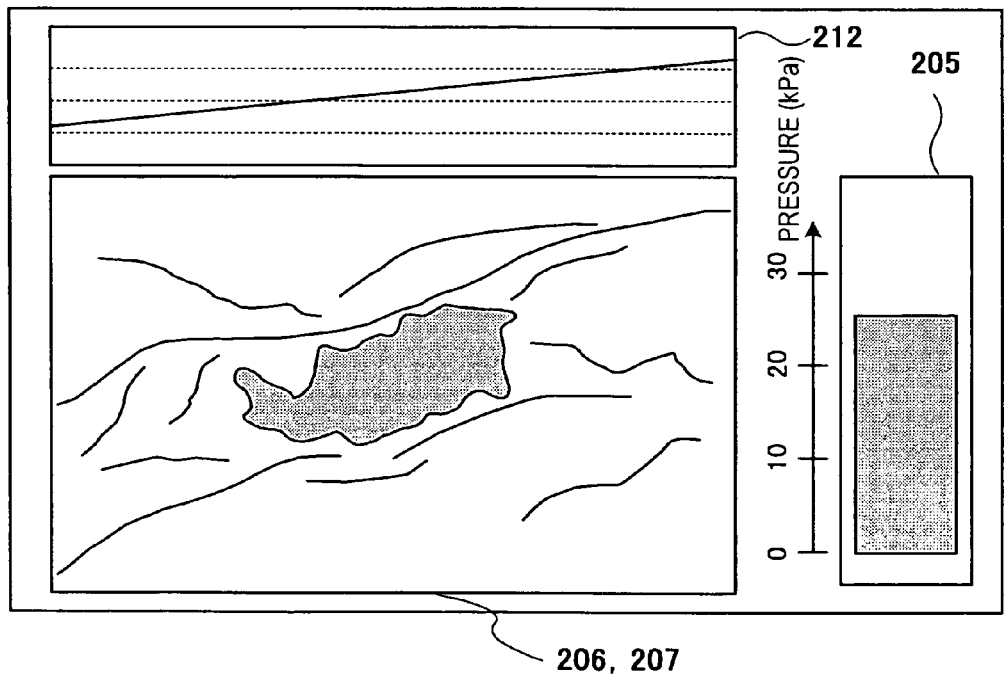
FIG. 25 illustrates an example in which a deviation with respect to a reference pressure of a pressure distribution in the long axis direction of an ultrasound transducer is represented as a line graph matching the coordinate direction corresponding to an elastic image.

For example, as shown in FIG. 25, the deviation of the pressure distribution with respect to a reference pressure may be determined, and the deviation may be displayed as a line graph 212 matching the coordinate direction of the elastic image corresponding to the long axis direction of the ultrasound transducer. In such a case, the bias in the compression force in the long axis direction of the ultrasound transducer can be immediately recognized by the image.

As measurement result data of the compression state determination unit 115, for example, a magnetic sensor may be provided on the ultrasound transducer 100, compression state image data may be generated using positional coordinate data output from the magnetic sensor, and the compression state image data may be displayed on the image display unit 107. Furthermore, compression speed data and displacement (vector) data derived from the positional coordinate data may also be displayed.

As measurement result data of the compression state determination unit 115, displacement information from the displacement measuring unit 109 may be used. More specifically, as measurement result data of the compression state determination unit 115, compression state image data may be generated using displacement frame data output from the displacement measuring unit 109. At this time, the data displayed on the image display unit 107 may be data of the average displacement, data that has been statistically processed, compression speed data computed on the basis of the displacement data, or integrated displacement data obtained by integrating the displacement data by time.

A plurality of images of compression state information may be simultaneously displayed on the image display unit. The diagnostic ultrasound system allows the examiner to freely select and set information configuring compression state image data, which is included in the plurality of information items, such as the displacement representing the compression state and the compression speed, through the system control interface unit 116. Here, the selected information item is not limited to one item and a plurality of items may be selected at the same time. When a plurality of information items is selected, the selected sets of compression state image data are configured as display image data and are simultaneously displayed on the image display unit 107.

According to the above-described embodiments, selecting whether or not to display a compression state image and setting the display range of the compression state image are freely controlled by the examiner using the system control interface unit 116.

As described in the embodiments above, according to the present invention, by providing the examiner with compression state information in association with an elastic image, highly objective elastic image diagnosis becomes possible.

Next, an example of the operation of the diagnostic ultrasound system according to all of the embodiments will be described. First, in accordance with ultrasound transmission and reception control, an ultrasonic wave is emitted to the probe 100 in contact with the body surface of the subject by applying a high-voltage electric pulse from the transmitting circuit 102, and a reflected echo signal from the region to be diagnosed is received by the probe 100. Next, the received signal is input to the phasing and adding circuit 104 after being input to the receiving circuit 103 and preliminarily amplified. The received signal whose phase is matched by the phasing and adding circuit 104 receives signal processing, such as compression and detection, at the following signal processor 105 and then is input to the monochrome scan converter 106. The monochrome scan converter 106 carries out A/D conversion of the received signal and stores the converted received signal in a plurality of frame memories in monochrome scan converter 106 as sets of chronologically consecutive cross-sectional image data.

Since RF signal frame data is continuously output from the phasing and adding circuit 104, the RF signal frame data selector 108 takes in the RF signal frame data in order. Among the RF signal frame data stored in the RF signal frame data selector 108, time-sequentially consecutive sets of RF signal frame data are selected by the RF signal frame data selector 108 and are taken in by the displacement measuring unit 109. Then, at the displacement measuring unit 109, a one-dimensional or two-dimensional displacement distribution ($\Delta L_{i, j}$) is determined. The calculation of the displacement distribution is carried out according to the above-mentioned method of detecting a movement vector, such as the block matching method. However, the method is not limited, and a generally used method in which autocorrelation in the same areas in two sets of image data is calculated to calculate the displacement may be employed.

At the pressure measuring unit 110, pressure applied to the body surface is measured by the pressure sensors, and the pressure data is sent from the pressure measuring unit 110 to the distortion and elasticity computing unit 111 and the compression state determination unit 115.

The measurement signals for the displacement ($\Delta L_{i,j}$) and the pressure ($\Delta P_{i,j}$) that are output from the displacement measuring unit 109 and the pressure measuring unit 110, respectively, are input to the distortion and elasticity computing unit 111, and the distortion amount distribution ($\epsilon_{i,j}$) is determined. The distortion amount distribution ($\epsilon_{i,j}$) is calculated by spatially differentiating ($\Delta L_{i,j}/\Delta X$) the displacement distribution ($\Delta L_{i,j}$). Moreover, Young's modulus $Y_{mi,j}$ included in the elasticity modulus is calculated by the following expression.

$$Y_{mi,j}=(\Delta P_{i,j})/(\Delta L_{i,j}/\Delta X)$$

The elasticity modulus of each measurement point is determined on the basis of the elasticity modulus $Y_{mi,j}$ determined in the way, and elastic frame data is generated.

Various types of image processing, such as smoothing in the coordinate plane, contrast optimization, and smoothing in the time axis direction between frames, are carried out at the elastic data processor 112 that received the elastic frame data. The compression state determination unit 115 evaluates the current compression state of the target tissue, configures compression sate image data including the evaluated compression state as information, and sends the compression state image data to the switching adder 114. The switching adder 114 simultaneously displays a monochrome cross-sectional image, a color elastic image, and a compression state image so that the relationship among these can be simultaneously observed.

As the formation of the above-described elastic image, an example in which elastic image data is generated by determining the distortion or Young's modulus Ym of the body tissue has been described. However, the present invention is not limited, and the elasticity modulus may be computed using other parameters, such as a stiffness parameter $\beta$, a compressive elasticity coefficient Ep, or an incremental elasticity coefficient Einc (JP5-317313A).

Figure 1:
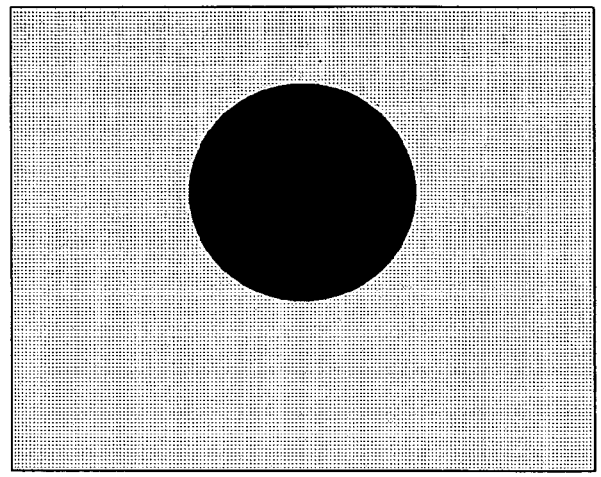
FIG. 1 illustrates that an elastic image depends on the level of compression.
Figure 1:
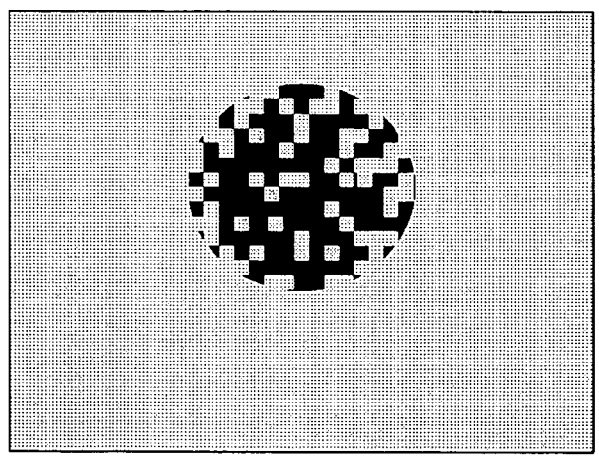
Figure 1:
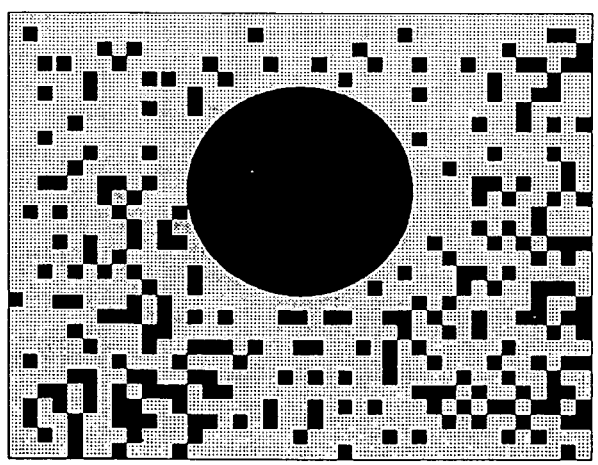

In the embodiment shown in FIG. 1, a case in which the probe 100 is in contact with the body surface of the subject 10 is described. However, the present invention is not limited and may be employed to any other ultrasound transducer, such as a transrectal probe, a transesophageal probe, an intraoperative probe, or an intravascular probe.

According to such configuration, for elastic image diagnosis by a diagnostic ultrasound system according to the present invention, a diagnostic ultrasound system that allows highly objective elastic image diagnosis is provided by displaying compression state information in association with an elastic image.

Figure 24:
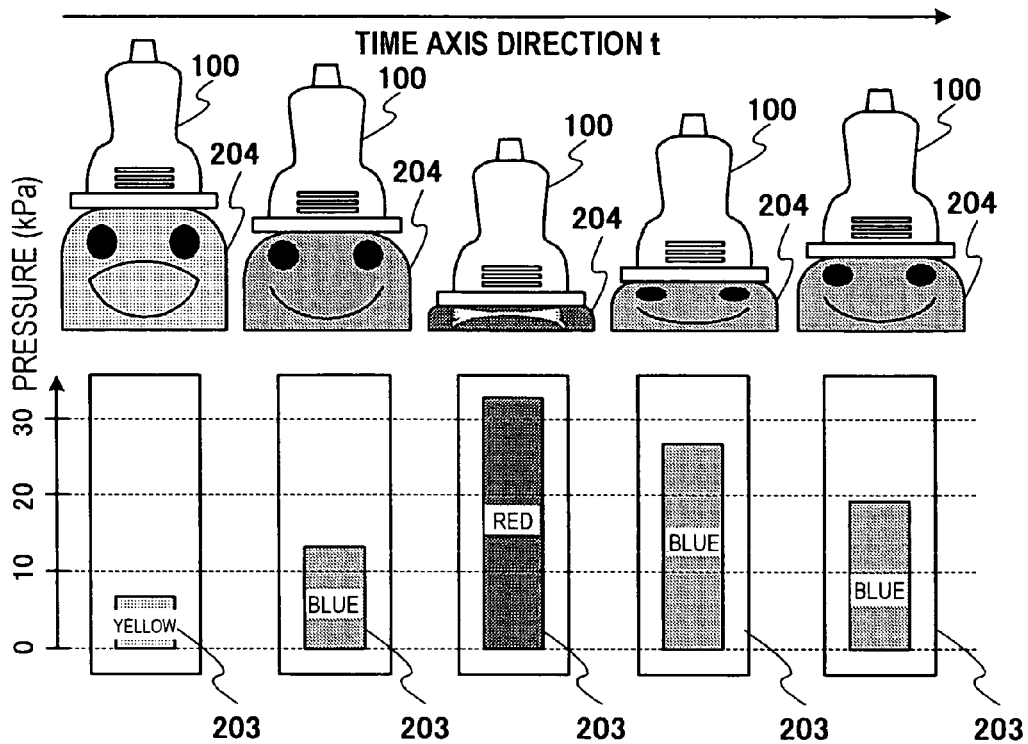
FIG. 24 illustrates another display example for when the pressure range is adequate, lacking, and excessive.

FIG. 8 illustrates a case in which the lengths of bar graphs representing the current compression state image data change over time in accordance with the compression strength applied to the target tissue and a case in which the state of the target tissue being compressed by the probe is schematically displayed. However, as shown in FIG. 24, eyes and a mouth may be schematically displayed on the target tissue, and the expression may be changed for adequate compression state, lacking of compression, and excessive compression. In the drawing, when compression is lacking, the mouth is opened to indicate that compression is lacking, and when compression is excessive, the mouth and eyes are tightly closed. In addition to the change in expression, colors may be used in the section of the target tissue, as shown in FIG. 18, to represent the cases such that blue represents that compression is adequate, red represents that compression is excessive, and yellow represents that compression is lacking.

Fifteenth Embodiment

In the above-described embodiments, a method of eliciting pressure data that represents the absolute strength of the current compression as compression state data. However, the present invention is not limited, and distribution of the pressure change can be displayed.

The displacement measuring unit 109 measures the displacement at each measurement point on the cross-sectional image from a pair of RF signal frame data sets selected at the RF signal frame data selector 108 and generates displacement frame data. The displacement is generated by changing the magnitude of the pressure applied to the living body. When a living body is compressed, the pressure change is in the positive direction, whereas when the living body is relaxed, the pressure change is in the negative direction.

Figure 26:
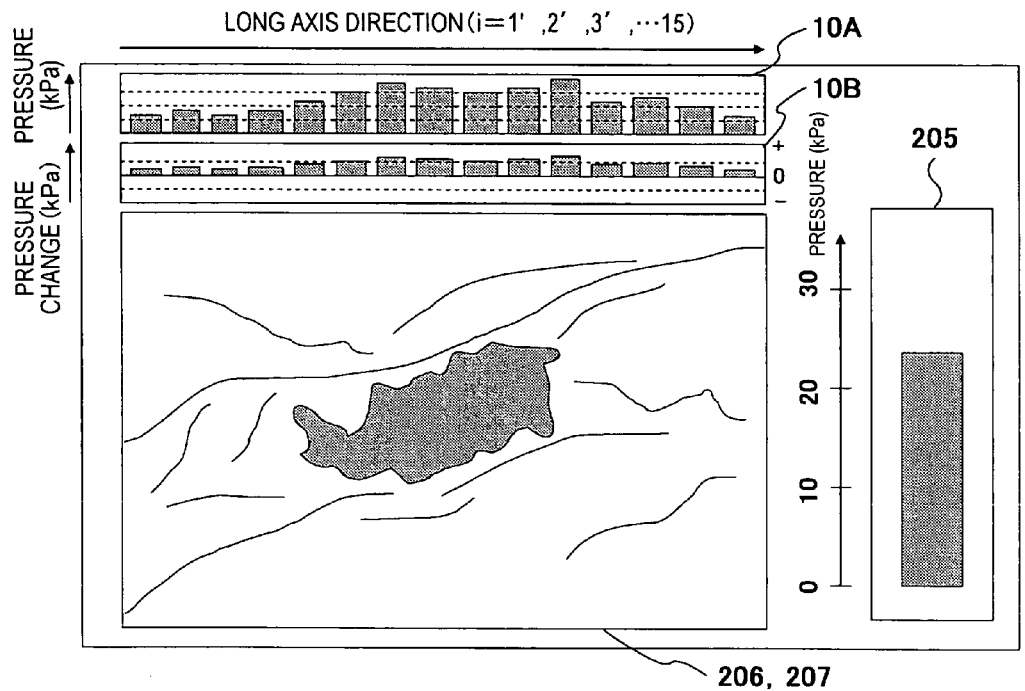
FIG. 26 illustrates an example in which an absolute pressure distribution in the long axis direction of an ultrasound transducer and a pressure change distribution of the change in the magnitude of pressure are represented by bar graphs corresponding to an elastic image.

In this embodiment, the change in the magnitude of the pressure in one frame is displayed as a pressure change distribution 10B. The pressure change distribution 10B is simultaneously displayed with an absolute pressure distribution 10A in real-time, for example, as shown in FIG. 26. Since the change in the magnitude of the pressure in one frame is slight, the graph of the pressure change distribution 10B enlarged more than the absolute pressure distribution 10A. By using a key of the system control interface unit 116, the pressure distribution to be displayed can be switched between the absolute pressure distribution and the pressure change distribution.

By displaying the pressure change distribution 10B as an image, it can be easily confirmed whether or not the elastic image displayed at the current time is generated by adequate compression operation.

Sixteenth Embodiment

Figure 27:
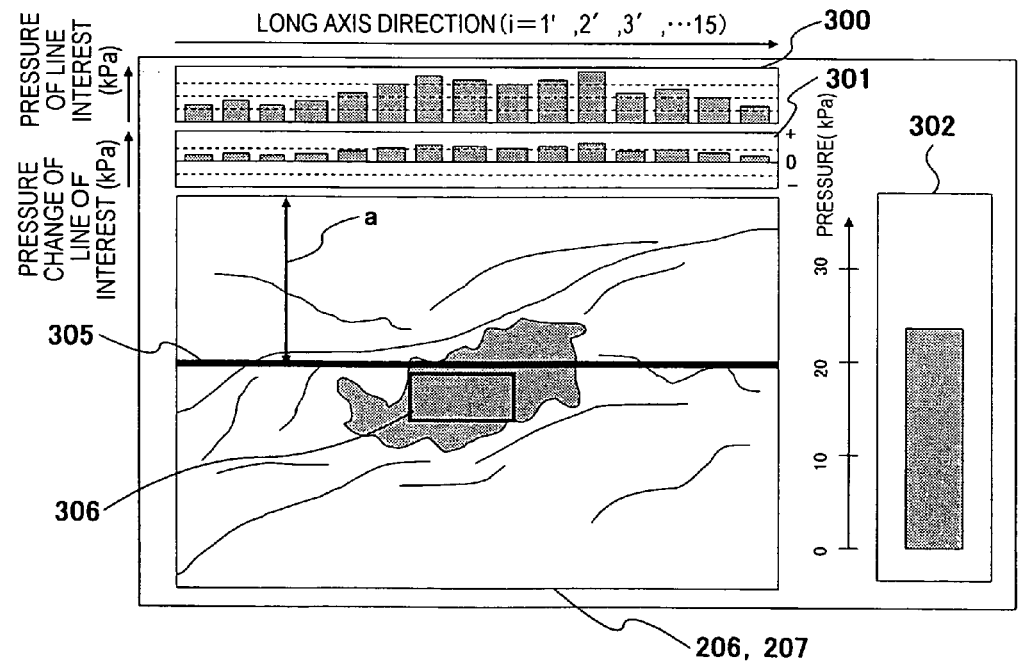
FIG. 27 illustrates an example in which the pressure distribution and the pressure change distribution in the long axis direction of an ultrasound transducer on a stress line of interest set on the image is represented by a bar graph corresponding to an elastic image.

As described above, the hardness of body tissue is non-linear, and the hardness of the tissue changes depending on the compression conditions. As shown in FIG. 27, a predetermined stress line of interest 305 is provided on the image, and a stress distribution 300 and a stress change distribution 301 following the line 305 are displayed.

The stress on the stress line of interest 305 for displaying the stress distribution 300 and the stress change distribution 301 is determined by a finite element method based on information such as the surface pressure, the properties of the substance, distortion, and the distance from the surface.

The finite element method is a known technology for numerical calculation. To carry out analysis when the target structure to be calculated is deformed by an external force applied by a probe, the target structure corresponding to the inside of the subject is sectioned with a mesh. Then, a system of linear equations is generated inside each small element. In the case according to this embodiment, the stress on the line is set as an unknown value, and an equation is formulated on the basis of information such as the surface pressure, the properties of the substance, distortion, and the distance from the surface. Each element of the equation is added together to formulate a system of linear equations, and the solution, which is the stress, is determined. Details of determining the solution is not described here since the details are described in publications, such as non-patent document "yugen yoso nyumon" written by Toshiro Miyoshi.

On the basis of the stress information determined by the finite element method, stress on the stress line of interest 305 is determined, and the stress distribution 300 is displayed. The change in the magnitude of stress in one frame is displayed as the stress change distribution 301. The stress change distribution 301 is, for example, as shown in FIG. 27, simultaneously displayed with the stress distribution 300 in real-time.

A predetermined stress region of interest 306 may be provided on the image, and the stress distribution and the change in stress in the stress region of interest may be measured. By employing the above-described finite element method, the magnitude of the stress and the change in stress before and after compression inside the stress region of interest are measured, and, for example, displayed as a bar graph 302.

According to these display methods, the stress applied to the affected region of interest can be directly examined, and even between different examiners, the distortion and the elasticity modulus of the affected tissue can be measured under stress conditions of the same magnitude. Thus, the elasticity modulus of body tissue presenting a non-linear response can be more definitively and objectively measured.

Figure 28:
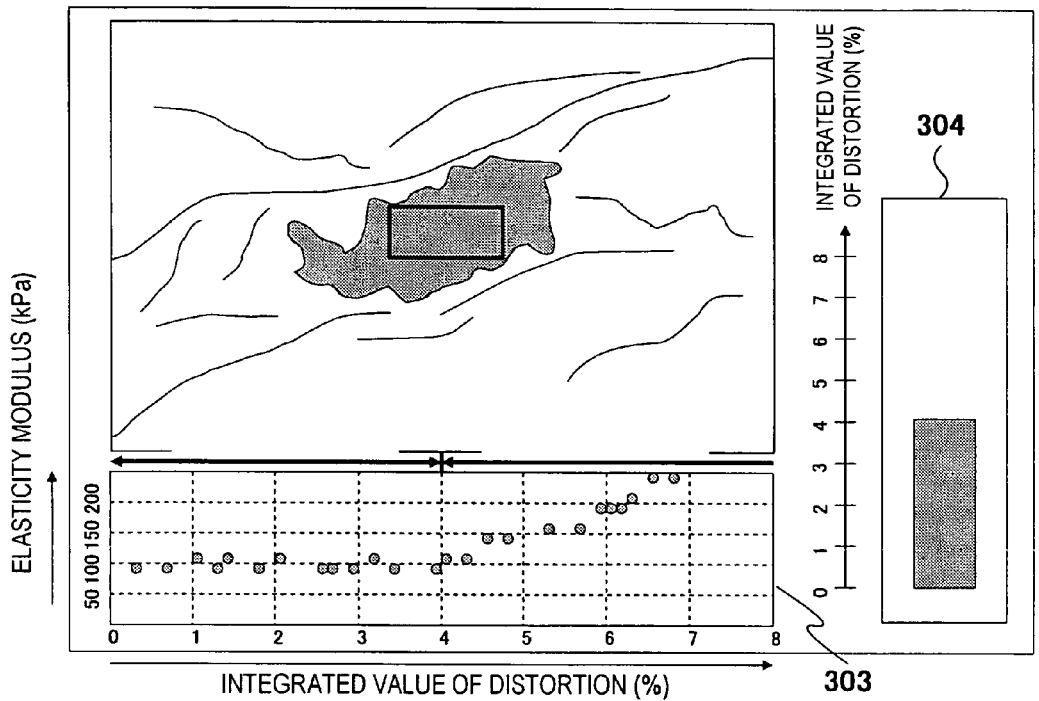
FIG. 28 illustrates an example in which the relationship between an integrated value of distortion and an elasticity modulus in a region of interest is displayed and the integrated value of distortion is represented by a bar graph.

In the description above, measurement conditions are standardized on the basis of the magnitude of the stress. However, the present invention is not limited, and an integrated value of distortion data may be measured and displayed. A configuration in which the integrated value of distortion is displayed in real-time is illustrated in FIG. 28. A distortion region of interest is set in the affected region, and the integrated value of distortion is measured by integration from a state of zero pressure and is displayed, for example, as a bar graph 304. The integrated value of distortion is a value that indicates how much compression has been carried out from the state of zero pressure. Accordingly, the relationship between the magnitude of the integrated value of distortion at the affected region and the elasticity modulus measured under the conditions can be grasped.

Here, at where the integrated value of distortion is about 4%, a separation into a linear region where the elasticity modulus is maintained at a constant value and a non-linear region where the elasticity modulus varies occurs. The non-linear region is generated by pressing the subject 10 too much and causing the subject 10 to not distort (to become hard). In the non-linear region, the elasticity modulus is considered as being unreliable.

Furthermore, the relationship between the distortion integrated value measured in the distortion region of interest and the elasticity modulus measured in the same region is chronologically represented by a graph 303. When the non-linear region is entered, it can be easily recognized that the elasticity modulus is not definitive. At this time, as shown in the drawing, when the non-linear region is entered with the distortion integrated value of the distortion region of interest exceeding, for example, 4%, a feedback (warning) may be provided as an image or audio to the examiner.

In the above, a method of identifying a non-linear response with reference to an integrated value of distortion is described. However, the value is not limited to an integrated value of distortion and, instead, a method based on the magnitude of stress may be employed in which appropriate information representing the state of compression may be the reference.

Seventeenth Embodiment

Figure 29A:
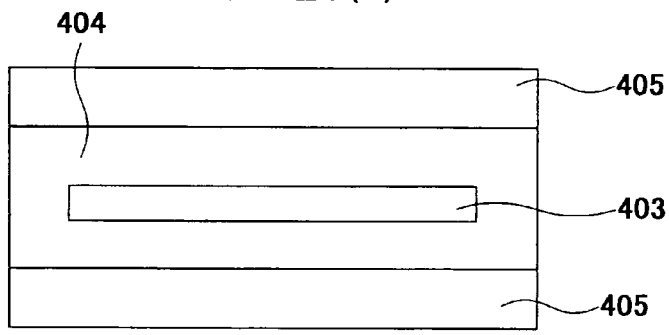
FIG. 29(a) is a cross-sectional view of a cMUT transducer.

A cMUT transducer employing MEMS technology or a device employing a liquid crystal touch panel is used as a pressure sensor. As shown in FIG. 29(a), the cMUT transducer generally includes a silicon member 404 sandwiching a vacuum gap 403 and electrodes 405 sandwiching the silicon member 404 and applying a bias voltage.

Here, when an ultrasound transducer provided with the cMUT transducer on the surface is contacted with the subject 10 and pressure is applied, the vacuum gap 403 is compressed in accordance with the pressure. This phenomenon is applied to measure the pressure. More specifically, the relationships of the deflection of the vacuum gap 403 and voltage and the relationship of the voltage and the pressure are stored in advance. For example, when the deflection of the vacuum gap 403 is 10 μm, the voltage changes by 5 V. When the pressure changes by 5 V, the pressure is 10 kPa. In such a manner, the surface pressure of the cMUT transducer can be measured through the vacuum gap 403.

Figure 29B:
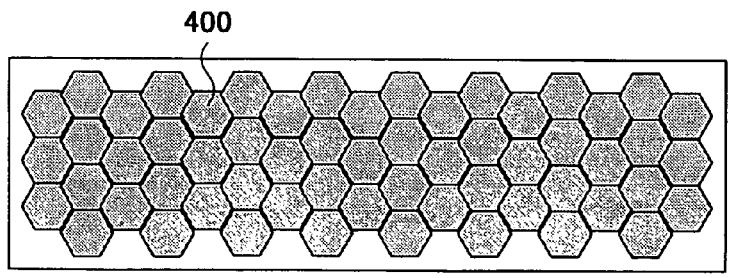
FIG. 29(b) is a plan view of a transducer being constituted of a plurality of cMUT transducers.

FIG. 29(b) illustrates the positions of cMUT transducers 400. The pressure at each cMUT transducer 400 can be calculated. The pressure in the region where the cMUT transducers 400 are disposed can be simultaneously measured.

Figure 29C:
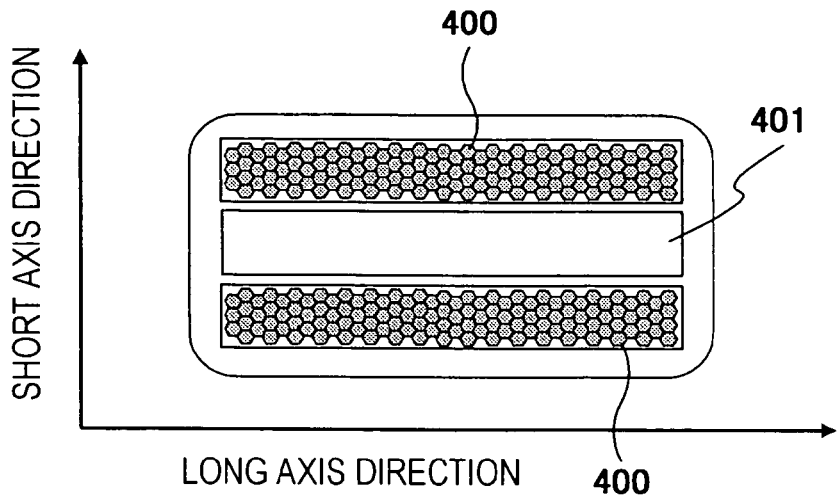
FIG. 29(c) is a block diagram of an ultrasound transducer in which cMUT transducers are disposed on both sides of an ultrasound transmission and reception surface.

FIG. 29(c) illustrates a configuration in which cMUT transducers are disposed on both sides of an ultrasound transducer 401. Similar to the example in FIG. 6, pressure can be measured. A touch panel may be fixed in the vicinity of the head of the ultrasound transducer 401.

Only the cMUT transducers may be aligned on the subject contact surface. By employing cMUT transducers according to MEMS technology that are capable of ultrasound transmission and reception and pressure measurement, pressure can be measured simultaneously with usual ultrasound diagnosis.

Eighteenth Embodiment

Figure 30:
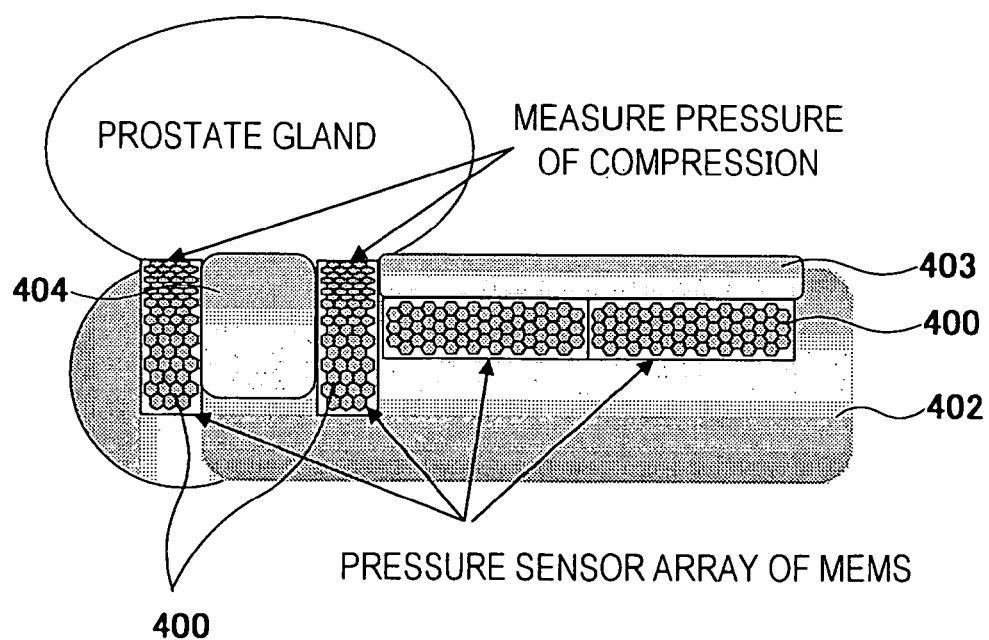
FIG. 30 illustrates an example of an ultrasound transducer used inside a body, employing pressure measurement means of a cMUT transducer.

Since the cMUT transducers and the touch panel can be constituted of thin devices, not only standard linear probes and convex probes may be constituted but also, as shown in FIG. 30, an ultrasound transducer 402 that can be inserted into the body, such as to the prostate gland, while applying less stress to the patient can be constituted and used to detect the pressure distribution.

In the ultrasound transducer used in the body 402, the linear transducer 403 and a curved transducer 404 are disposed at two different positions. On both sides of the transducers, the cMUT transducers 400 are aligned. The cMUT transducers are aligned linearly in the vicinity of the linear transducer 403 and are arranged as on the surface of a mountain in the vicinity of the curved transducer 404. The cMUT transducers 400 are positioned in the same direction as the scanning direction of the ultrasound signal. By aligning the cMUT transducers 400 in this way, pressure can be appropriately measured. The alignment of the cMUT transducers 400 is not limited to this arrangement and instead, may surround the transducers. Then, the pressure is measured in a way similar to the method according to the seventeenth embodiment. In other words, the ultrasound transducer used in the body 402 is capable of displaying a compression state images of the bar graph 201 corresponding to the pressure value and the pressure change line graph 210.

Only the cMUT transducers 400 may be aligned on the compression surface to measure pressure simultaneously with the above-described standard ultrasound diagnosis.

Nineteenth Embodiment

Figure 31A:
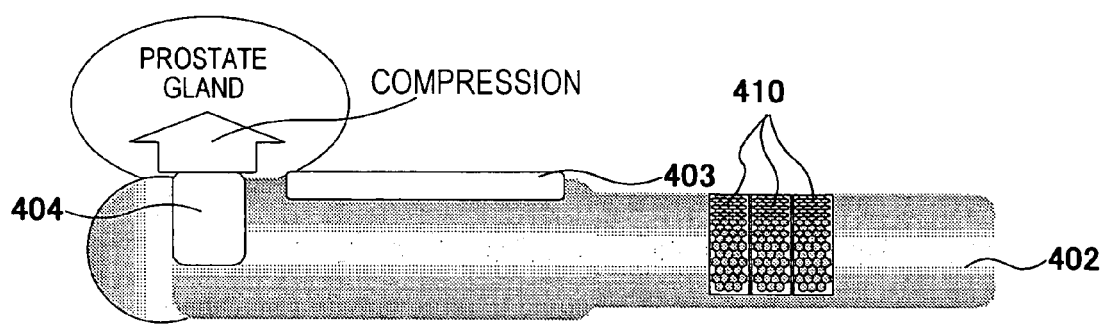
FIG. 31(a) illustrates another example of an ultrasound transducer used inside a body, employing pressure measurement means of a cMUT transducer.
Figure 31B:
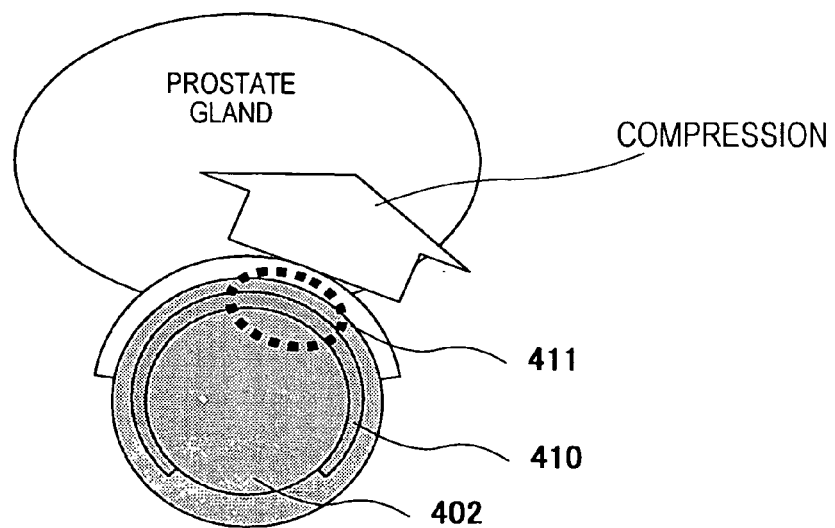
FIG. 31(b) illustrates the operation of the ultrasound transducer used inside a body shown in FIG. 31(b).

On the handle of the ultrasound transducer used in the body, sensors for detecting stretching and deflection may be provided so that the probe can be used as a pressure sensor. As shown in FIG. 31, sensors 410 for detecting stretching and deflection, such as touch panel technology, MEMS technology (cMUT transducers), or distortion gauge, are attached to a section of the handle of the probe. The attachment position may be far away from the head. The distortion gauge may be electrical or optical.

By compressing the prostate gland, a section of the handle of the ultrasound transducer used in the body 402 is deflected. The deflection is measured by the pressure sensors provided on the handle. More specifically, a pressure sensor 410 is disposed in a manner such that all directions of the curved transducer 404 are covered. Then, the relationship of the displacement in the bias voltage caused by expansion (deflection) in the section of the handle or distortion of the cMUT transducers and the pressure at the tip of the ultrasound transducer used in the body is stored in advance, and the pressure is measured in association with the expansion of the region. In the configuration shown in FIG. 31(b), a region 411 in the same direction as the compression direction expands in the long axis direction. This phenomenon is measured with the above-described pressure sensors, the pressure and the compression direction are calculated, and the pressure and the compression direction are displayed on a screen.

Accordingly, by analyzing the pressure distribution obtained by the array of the above-described sensors, the pressure and the compression direction can be determined. Furthermore, the same result can be achieved by disposing a plurality of distortion gauges in an arc-shape.

The above-described sensors are provided as a unit that can be easily attached and detached. They can be easily employed to a probe that is inserted into the body, such as transrectal, transvaginal, or transesophageal endoscope probe. According to the method of detecting the bending, the sensors do not have to be inserted into the body, and safe measurements can be carried out without applying stress to the patient.

The invention claimed is:

1. A method of displaying an elastic image comprising the steps of:
   (a) measuring ultrasound cross-section data of a cross-section region of a subject;
   (b) determining a distortion value of tissue in the cross-section region of the subject on the basis of the ultrasound cross-section data;
   (c) generating an elastic image of the cross-section region of the subject on the basis of the distortion value and displaying the elastic image on a display device;
   (d) determining compression state information relating to the compression state of the cross-section region of the subject on the basis of the pressure applied to the subject; and
   (e) displaying the compression state information together with the elastic image on the display device;
   wherein the compression state information is determined by integrating the distortion value of the tissue of the cross-section region of the subject with respect to time from a state of zero pressure applied to the subject.

2. The method of claim 1, wherein the compression state information displayed on the display device changes in accordance with a change over time of the pressure applied to the subject.

3. The method of claim 1, further comprising the steps of:
   determining whether or not the pressure applied to the subject is within a set range on the basis of the compression state information; and
   outputting at least one of audio and image display as an alert when the pressure is not within the set range.

4. The method of claim 1, wherein,
   the pressure applied to the subject is applied through an ultrasound transducer used in contact with the subject,
   the compression state information is pressure distribution data determined in association to a long axis direction of a plurality of transducers constituting the ultrasound transducer, the long axis direction being the alignment direction of the plurality of transducers, and
   the pressure distribution data is displayed on the display device as a bar graph or a line graph matching a coordinate direction corresponding to the long axis direction of the elastic image.

5. The method of claim 4, further comprising the steps of:
   determining the deviation with respect to a reference pressure of the pressure distribution data; and
   displaying the deviation on the display device as a line graph matching the coordinate direction corresponding to the long axis direction of the elastic image.

6. The method of claim 1, wherein,
   the pressure applied to the subject is applied through an ultrasound transducer used in contact with the subject,
   the compression state information is at least one set of pressure data of an average value, a variance value, a median value, a maximum value, and a minimum value of a pressure distribution determined in association with a long axis direction of a plurality of transducers constituting the ultrasound transducer, the long axis direction being the alignment direction of the plurality of transducers, and
   the pressure data is juxtaposed to the elastic image and is displayed on the display device.

7. The method of claim 6, wherein the pressure data is at least one of
   a numerical value,
   a bar graph having a length corresponding the numerical value,
   a graphic representation having brightness or color corresponding to the numerical value,
   a bar graph having a length corresponding to the numerical value and having brightness or color corresponding to the numerical value,
   a simulation meter representing the numerical value with a rotational angle of a needle,
   a circular graphic representation having a diameter equal to the numerical value, and
   a graphic representation representing the numerical value by simulating the state of compression and deformation of the cross-section region.

8. The method of claim 1, further comprising the steps of:
   measuring the ultrasound cross-section data by repeatedly changing the pressured applied to the subject;
   determining the change in the pressure applied to the cross-section region; and
   displaying a pressure change line graph representing the change over time in the pressure together with the elastic image on the display device.

9. The method of claim 8, further comprising the step of:
   displaying a reference line graph on the display device in an overlapping manner on the pressure change line graph, the reference line graph being an example of a change over time of the pressure being applied to the cross-section region.

10. The method of claim 8, wherein, when displaying the pressure change line graph and the elastic image read out from a cine memory storing the pressure change line graph and the elastic image on the display device and when a mark is displayed on a time axis of the pressure change line graph and moved along the time axis, an elastic image corresponding to the time indicated by the mark is read out from the cine memory and is displayed.

11. The method of claim 8, further comprising the steps of:
freezing the pressure change line graph representing the change over time of the pressure and the elastic image;
setting a start point and an end point of one cycle of the pressure change on the pressure change line graph; and
storing the pressure change line graph corresponding to the set one cycle and the elastic image.

12. The method of claim 11, wherein the start point and the end point of the one cycle of the pressure change is automatically set.

13. The method of claim 1, wherein the compression state information includes a pressure change distribution of a change in one frame of the pressure applied to the subject.

14. The method of claim 1, further comprising the step of:
setting one of a stress line of interest and a region of interest on the elastic image displayed on the display device,
wherein the compression state information includes a stress change distribution along the stress line of interest of the change in one frame of stress applied to the subject and a stress change distribution included in the range of interest.

15. The method of claim 1, further comprising the steps of:
determining a distortion integrated value of the tissue the cross-section region as the physical value,
wherein the compression state information includes the distortion integrated value.

16. The method of claim 1, further comprising the step of:
applying the pressure to be applied to the subject through an ultrasound transducer used in contact with the subject,
wherein the pressure is measured by a cMUT transducer provided on the ultrasound transducer.

17. The method of claim 1, further comprising the step of:
applying the pressure to be applied to the subject through an ultrasound transducer used by being inserted into the subject,
wherein the pressure is measured by a pressure sensor provided on the ultrasound transducer.

18. A diagnostic ultrasound system comprising:
(a) a signal processor configured to generate a cross-sectional image and an elastic image by processing a signal detected by an ultrasound transducer in contact with a subject;
(b) pressure detecting means for determining the pressure applied to the subject;
(c) compression state evaluation means for evaluating a compression state of the subject; and
(d) a display on which compression state information evaluated by the compression state evaluation means is displayed in association with the elastic image,
wherein the compression state evaluation means is configured to determine the compression state information by integrating a physical value of tissue of a cross-section region of the subject with respect to time from a state of zero pressure applied to the subject.

19. The system of claim 18, wherein,
the pressure detecting means includes at least one pressure sensor disposed in the vicinity of a contact surface of the subject and the ultrasound transducer, and
the compression state evaluation means generates the compression state information by carrying out statistical processing on the pressure data from the pressure sensor.

20. The system of claim 19, wherein the compression state information is a combination of a numerical value corresponding to the pressure data and a unit of pressure.

21. The system of claim 19, wherein the pressure sensor is aligned along a long axis direction of ultrasound transmission and reception.

22. The system of claim 19, wherein the pressure sensor is a reference deforming body for measuring pressure applied to a body surface.

23. The system of claim 19, wherein the pressure sensor is a group of a plurality of pressure sensors disposed along a short axis direction of a ultrasound transmission and reception surface.

24. The system of claim 18, wherein;
the compression state information is at least one set of pressure data of an average value, a variance value, a median value, a maximum value, and a minimum value of a pressure distribution determined in association with a long axis direction of a plurality of transducers constituting the ultrasound transducer, the long axis direction being the alignment direction of the plurality of transducers, and
the pressure data is juxtaposed to the elastic image and is displayed on the displaying means.

25. The system of claim 19, wherein the pressure data is at least one of:
a numerical value,
a bar graph having a length corresponding the numerical value,
a graphic representation having brightness or color corresponding to the numerical value,
a bar graph having a length corresponding the numerical value and having brightness or color corresponding to the numerical value,
a simulation meter representing the numerical value with a rotational angle of a needle,
a circular graphic representation having a diameter equaling the numerical value, and
a graphic representation representing the numerical value by simulating the state of compression and deformation of the cross-section region.

26. The system of claim 18, wherein the compression state information is a pressure change line graph representing the change over time of the pressure applied to the subject.

27. The system of claim 26, wherein the pressure state evaluation means displays a reference line graph on the displaying means in an overlapping manner on the pressure change line graph, the reference line graph being an example of a change over time of the pressure being applied to the subject.

28. The system of claim 26, wherein:
a predetermined section is set, and
the set pressure change line graph and the elastic image are stored on a storage medium.

29. The system of claim 26, wherein a compressed section is extracted.

30. The system of claim 26, wherein;
a magnetic sensor is provided on the ultrasound transducer, and
compression state image data is generated and displayed using positional coordinate data output from the magnetic sensor.

31. The system of claim 26, further comprising:
a cine memory for storing the pressure change line graph and the elastic image; and
control means for controlling the cine memory,
wherein the control means displays a mark on a time axis of the pressure change line graph when the pressure change line graph and the elastic image being read out from the cine memory are displayed on the displaying means, and an elastic image according to the time indicated by the mark is read out from the cine memory and is displayed when the mark is moved along the time axis.

32. The system of claim 31, wherein the mark is controlled in a sliding manner in the time axis direction.

33. The system of claim 26, wherein the control means freezes the pressure change line graph and the elastic image, sets a start point and an end point of one cycle of the pressure change on the pressure change line graph, and stores the pressure change line graph corresponding to the set one cycle and the elastic image on a recording medium.

34. The system of claim 32 or 33, wherein the stored image data is played back for a set section.

35. The system of claim 33, wherein the control means automatically sets the start point and the end point of the one cycle of the pressure change.

36. The system of claim 18, wherein the compression state evaluation means determines whether or not the pressure applied to the subject is within a set range and outputs at least one of audio, a graphic representation, and colors as an alert when the pressure is not within the set range.

37. The system of claim 18, wherein the compression state information includes a pressure change distribution of the change in one frame of pressure applied to the subject.

38. The system of claim 18, further comprising:
input means for setting one of a stress line of interest and a region of interest on the elastic image displayed on the displaying means,
wherein the compression state evaluation means determines a stress change distribution along the stress line of interest of the change in one frame of stress applied to the subject and a stress change distribution includes in the range of interest.

39. The system of claim 18, wherein the compression state evaluation means determined a distortion integrated value of the tissue of the cross-section region as compression state information.

40. The system of claim 18, wherein the compression detection means is a cMUT transducer disposed in the vicinity of the contact surface of the ultrasound transducer and the subject.

41. The system of claim 18, wherein:
the pressure applied to the subject is applied through an ultrasound transducer used by inserting into the subject, and
the pressure detecting means is provided on the ultrasound transducer.

* * * * *